US011640850B2

(12) United States Patent
Minati et al.

(10) Patent No.: US 11,640,850 B2
(45) Date of Patent: May 2, 2023

(54) SYSTEM TO COMPARE AT LEAST ONE DNA FRAGMENT TO A REFERENCE GENOME

(71) Applicant: in2H2, Folsom, CA (US)

(72) Inventors: Ludovico Minati, Gringo (IT); Mickey Lee Fandrich, Oregon City, OR (US)

(73) Assignee: IN2H2, Folsom, CA (US)

( * ) Notice: Subject to any disclaimer, the term of this patent is extended or adjusted under 35 U.S.C. 154(b) by 1200 days.

(21) Appl. No.: 16/302,542

(22) PCT Filed: May 16, 2017

(86) PCT No.: PCT/US2017/032906
§ 371 (c)(1),
(2) Date: Nov. 16, 2018

(87) PCT Pub. No.: WO2017/201050
PCT Pub. Date: Nov. 23, 2017

(65) Prior Publication Data
US 2019/0221288 A1 Jul. 18, 2019

(30) Foreign Application Priority Data
May 19, 2016 (IT) .................. 102016000051318

(51) Int. Cl.
G16B 30/10 (2019.01)
G11C 19/28 (2006.01)
G06F 15/78 (2006.01)
C12Q 1/6869 (2018.01)
H03M 1/28 (2006.01)
G16B 30/20 (2019.01)
G16B 30/00 (2019.01)
G06F 13/16 (2006.01)
G06F 13/42 (2006.01)
G06F 5/01 (2006.01)
G11C 19/18 (2006.01)
G11C 7/10 (2006.01)
G11C 11/41 (2006.01)
G11C 19/00 (2006.01)
H03K 19/21 (2006.01)

(52) U.S. Cl.
CPC .......... G16B 30/10 (2019.02); C12Q 1/6869 (2013.01); G06F 13/1668 (2013.01); G06F 13/4282 (2013.01); G06F 15/7821 (2013.01); G11C 19/287 (2013.01); G16B 30/00 (2019.02); G16B 30/20 (2019.02); H03M 1/285 (2013.01); G06F 5/01 (2013.01); G06F 2213/0026 (2013.01); G06F 2213/0042 (2013.01); G11C 7/1006 (2013.01); G11C 7/1036 (2013.01); G11C 11/41 (2013.01); G11C 19/00 (2013.01); G11C 19/184 (2013.01); H03K 19/21 (2013.01)

(58) Field of Classification Search
None
See application file for complete search history.

(56) References Cited

U.S. PATENT DOCUMENTS

| 5,724,253 A | 3/1998 | Skovira |
| 2005/0267693 A1 | 12/2005 | Allard et al. |
| 2012/0191366 A1 | 7/2012 | Pearson et al. |

FOREIGN PATENT DOCUMENTS

| RU | 2375458 C2 | 12/2009 |
| WO | WO-2017201050 A1 | 11/2017 |

OTHER PUBLICATIONS

"International Application Serial No. PCT US2017 032906, International Preliminary Report on Patentability dated Nov. 29, 2018," 6 pgs.
"International Application Serial No. PCT/US2017/032906, International Search Report dated Aug. 24, 2017", 2 pgs.
"International Application Serial No. PCT/US2017/032906, Written Opinion dated Aug. 24, 2017", 4 pgs.

Primary Examiner — G Steven Vanni
(74) Attorney, Agent, or Firm — Schwegman Lundberg & Woessner, P.A.

(57) ABSTRACT

A computer system and method for sequencing deoxyribonucleic acid (DNA), to determine the order of the different nucleotides in a genomic sequence or sequence fragment. An alignment system employs a direct "brute force" Hamming distance calculation between a read sequence and a reference genome. The alignment system is configured to compare directly a set of DNA fragments to a reference genome in a short period, and with the higher probability of accuracy than similar comparison systems given the same number of clock cycles. Each DNA fragment is compared with a reference genome for the entire length of the latter using arrangements of memory cells for storing read sequences and inverse complements of the read sequences, shift registers for streaming the reference genome, and circuitry for calculating and summing the distance between the reference, the read sequence, and the inverse complement in parallel. Both digital and analog implementations are described.

18 Claims, 13 Drawing Sheets

SYSTEM TO COMPARE AT LEAST ONE DNA FRAGMENT TO A REFERENCE GENOME

This patent application is a U.S. National Stage Filing under 35 U.S.C. 371 from International Application No. PCT/US2017/032906, filed on May 16, 2017, and published as WO 2017/201050, which claims the benefit of priority to Italian Application Serial No. 102016000051318, filed May 19, 2016, which are incorporated by reference herein in their entireties.

The disclosed system pertains to the field of "biotechnology," technologies applied to biological systems, and sometimes, but not limited to, carrying out genetic-molecular analyses. The biotechnology industry in which the presently described system finds application is, more precisely, the "sequencing of biopolymers," the set of operations aiming to determine the primary structure of a biopolymer. For example the most frequently sequenced biopolymers include nucleic acids and proteins.

The disclosed system is related, in particular, to the sequencing of deoxyribonucleic acid (DNA), which is a type of sequencing aiming to determine the order of the different nucleotides (adenine, cytosine, guanine and thymine) in a genomic sequence or fragment of such sequence. For example, in the context of the human genome, knowledge of the order of nucleotides is useful to diagnose genetic diseases or identify other hereditary characteristics.

DNA sequencing procedures include multiple steps, the first of which generally consists in the genetic material (DNA) from a cell whose genetic makeup one seeks to examine. Said DNA sequence is then amplified (for example, by the "polymerase chain reaction" technique, or PCR) and subsequently cut randomly into fragments (usually called "reads"), each of which contains a variable number of nucleotides depending on the technology used, preferably on the order of hundreds of nucleotides, or more. To reconstruct the underlying sequence, the DNA fragments are aligned by comparing the nucleotides of each fragment with those of a reference genome. The operation of alignment is extremely complex from a computational point of view, because of the non-exact match expected between the DNA to be sequenced and the reference genome, and because the DNA fragments, obtained according to the aforesaid amplification process, can overlap wholly or in part. The number of possible alignments is also extremely large because the reference genome, for example the human genome, has a "length" on the order of billions of nucleotides.

In the present description, the expression "system for realignment of DNA fragments to be sequenced" shall refer to a system that produces as output a nucleotide sequence having the highest probability of matching the sequenced DNA.

Said alignment system in turn includes a comparison system meant to compare each DNA fragment with a reference genome for the entire length of the latter.

The output of the comparison system for each DNA fragment is a measure of how different the fragment is from each stretch of the reference genome with which it was compared. The difference is quantified in terms of number of different nucleotides, irrespective of the inequality between nucleotides. The number of different nucleotides is identified by the expression "Hamming distance". Based on the Hamming distances measured by the comparison system, other components of the alignment system determine the position (usually called "match," or "alignment") along the reference genome most likely corresponding to the first nucleotide of the fragment in question.

The disclosed system refers to a type of the aforementioned comparison system. The comparison between each DNA fragment and the reference genome can be carried out in a direct way or by means of indirect search methods based, for example, on Hash tables, indexes, trees and similar structures. The calculation of the Hamming distance in a direct way is usually called "brute force calculation" and provides exact results. Indirect methods instead provide approximate results whenever there is no exact match between a DNA fragment and a reference genome tract.

The disclosed system refers, more specifically, to an architecture that makes it possible to calculate the Hamming distance in a direct way for each possible alignment of a given DNA fragment, in a time shorter than that yielded by sequential execution on standard computer processors.

Review of Prior Art

The current comparison systems that calculate the Hamming distance by brute force compare each DNA fragment with all possible stretches of the reference genome having the same length of the fragment to be aligned, starting from a first nucleotide of the reference genome. More precisely, each nucleotide of the fragment to be aligned is compared with the nucleotide of reference genome in the corresponding location. The number of differing nucleotides is then calculated. The number thus obtained corresponds to the above defined Hamming distance and, as previously mentioned, is an indication of the mismatch between the fragment to be aligned and the reference genome stretch taken into account. A Hamming distance with a value of zero indicates an exact match between the fragment to align and the reference genome stretch. Once the aforesaid distance is measured, the fragment to be aligned is compared with the next stretch of the reference genome, with the stretch obtained by scrolling the reference genome by one nucleotide. This operation is repeated, for all the DNA fragments to be aligned, until the second end of the reference genome is reached. In this way, each DNA fragment is thus compared to the entire reference genome, producing a vector whose elements are the Hamming distances between the DNA fragment and the stretches of the reference genome to which it was compared.

It is noted that the DNA is composed of a pair of strands welded to one another, each consisting of a sequence of nucleotides. The nucleotides present in the two strands are coupled according to a predetermined rule: adenine is coupled to thymine and cytosine is coupled to guanine. As they are complementary, the two strands contain the same genetic information. The DNA fragments to be aligned are fragments of either of the two strands. Similarly, the reference genome consists of one of the two strands. Based on the sequencing technology prevalently in use nowadays, the DNA fragments are read in opposite directions depending on whether they belong to one or the other strand. However, one cannot know in advance what strand they belong to. Consequently, for each DNA fragment there is a double comparison to be made. In other words, the above procedure must be repeated twice: each DNA fragment needs to be compared both with the reference genome, and with its complement (the genome in which each nucleotide is replaced by its complement) read in reverse order.

The example shown below facilitates understanding the way in which the comparison described above is performed.

Let us consider that a reference genome comprises in order the following six nucleotides: A (adenine), C (cytosine), G (guanine), T (Thiamine) A G. Let us consider also a DNA fragment to align comprising the following three nucleotides: G T A. It is assumed that the reference genome should be read "ACGTAG" (and not "GATGCA") and that the fragment to be aligned should be read "GTA" (and not "ATG").

The comparison system compares the fragment "GTA" with the first stretch of three nucleotides in the reference genome ("A C G"), and calculates the distance between the two (equal to three).

The comparison system then scrolls the reference genome by a nucleotide, compares the fragment "GTA" with the second stretch of three nucleotides ("CGT"), and calculates the distance between the two (equal to three). The comparison system then again scrolls the reference genome of a nucleotide, compares the "GTA" fragment with the third stretch of three nucleotides (bones "GTA"), and calculates the distance between the two (equal to zero).

The comparison system scrolls one last time the reference genome by a nucleotide, compares the "GTA" fragment with the fourth stretch of three nucleotides (bones "TAG"), and calculates the distance between the two (equal to three).

The comparison between the DNA fragment and the reference genome has therefore produced a first vector of four elements containing the values of the four Hamming distances measured respectively during the four comparisons described above. The elements of this vector are: 3 3 0 3.

In the case in which the DNA to be sequenced comprises two strands, the comparison system creates a complement reference genome that, for biochemical reasons, must be read in reverse order, "CTACGT."

In a way equivalent to that described above, the comparison system then compares the "GTA" fragment with four stretches of the complementary genome and produces a second vector of four elements containing the values of the four distances respectively measured during the four comparisons. The elements of this second vector are: 1 3 3 3.

The comparison described above is repeated for all DNA fragments to be aligned. For each fragment, two distance vectors are produced, which are used by other components of the alignment system to calculate the sequence of nucleotides having the highest probability of matching the DNA being sequenced.

An example of a comparison system that implements, in part, the process described above is the object of U.S. Pat. No. 5,724,253. In said comparison system given nucleotides of the reference genome and of the DNA fragments to be aligned are stored in two-bit memory cells. Two bits are sufficient to identify the different types of nucleotides, the latter being equal to four. The comparison between two nucleotides belonging to a nucleotide fragment to be aligned and to the reference genome occurs by means of two exclusive OR (XOR) gates, each of which compares one bit and whose outputs are in turn connected to the inputs of an OR gate that produces a result equal to 1 if the nucleotides are different, and 0 if the nucleotides are equal. An adder sums the output values from these OR gates on the comparison of a DNA fragment and a stretch of equal length of the reference genome. The output value from the adder corresponds to the Hamming distance between the fragment to align and said reference genome tract.

The comparison system object of the U.S. Pat. No. 5,724,253 does not, however, involve comparison of each DNA fragment with a complement genome to that of reference read in reverse order. In addition to that, the high number of operations which must be performed to make a direct comparison between each DNA fragment and the reference genome renders calculating the Hamming distance in brute force by means of programs executed sequentially on a traditional processor too onerous from a computational point of view, requiring excessive execution time.

To overcome this drawback, nowadays the tendency is to employ almost exclusively the previously mentioned comparison systems that compare each fragment of DNA with the reference genome in an indirect way. The systems of this type employ algorithms with more favorable computational complexity which are based, primarily, on the Burrows-Wheeler Transform (BWT) and the index of Ferragina-Manzini (FM-index), as they are, for example, implemented inside the Bowtie program. In general, they rely upon abstracted representations of the reference genome, such as tables of indices or trees, such as to make the comparison of a given fragment of DNA less costly compared to the calculation of the Hamming distance in brute force. The comparison systems that use indirect search methods, however, provide approximate results whenever there is not an exact match (one with Hamming distance of zero) between a DNA fragment and at least a stretch of the reference genome. These systems also do not guarantee that they find all possible alignments corresponding to a given Hamming distance, unless the algorithms are applied iteratively. A DNA fragment can in fact align equally well to more than one location of the reference genome.

In summary, the indirect methods are currently used exclusively in response to a practical constraint associated with excessive brute force calculation time; however, their potential lack of accuracy is a substantial problem for the validation of the obtained results.

The disclosed system overcomes or minimizes the aforesaid drawbacks by indicating a comparison system able to compare directly (in an exact way, by means of brute force calculation) a set of DNA fragments to a reference genome in a shorter period of time than current similar comparison systems given the same number of clock cycles.

The present disclosure is a system suitable for comparing at least a fragment of DNA with a reference genome, characterized by the fact that it comprises:

at least a first computational and storage array including:

a plurality of pairs of shift registers each of which comprising a first row of one-bit memory cells, said first rows of each pair of registers being suitable for housing a first sequence of bit pairs encoding a sequence of nucleotides of the reference genome;

a plurality of pairs of second rows of one-bit memory cells addressable individually for writing and reading, each pair of second rows being suitable for housing a second sequence of bit pairs encoding a sequence of nucleotides of said DNA fragment;

a plurality of third lines of first digital equality comparators between bit pairs, each of the first comparators being suitable for comparing a bit pair of the first sequence with a bit pair of the second sequence, said first comparators belonging to the same third line being suitable for comparing bit pairs of the same first sequence with bit pairs of the same second sequence;

for each third line, at least a first adder of the output signals from at least two of the first comparators belonging to said third line, each first adder being suitable for generating an output signal encoding a value corresponding to a first distance between at least a fragment of the first sequence and a corresponding stretch of the second sequence compared by the first comparators, whose said output signals are input into said first adder;

at least a second adder of two or more of said first distances suitable for generating an output signal encoding a value corresponding to a second distance;

at least a second comparator suitable for comparing said second distance with a threshold value;

a processor suitable for controlling the operation of writing or reading in the memory cells of the second rows, and controlling the operation of the pairs of shift registers, of the first comparator, second comparator, first adder and second adder.

Further innovative characteristics of the disclosed system are described in the claims.

In the present description, for convenience of presentation, reference is made only to an example of the disclosed system, wherein the comparison system is employed for aligning DNA fragments. However, the system is not limited to the above example. It can be used, in an equivalent manner, for aligning fragments of any polymer, such as fragments of ribonucleic acid (RNA). More generally, the disclosed system can be used, in an equivalent manner, for comparing strings of symbols with a reference string comprising given symbols. It is sufficient that the number of bits (and with it the number of XOR gates and the width of the OR gate to which said gates are connected) is appropriately increased to represent the possible elements. For example, 6 bits are sufficient to represent the 64 possible codons in protein synthesis.

In the light of the above, in the present text, the expression "DNA fragments" refers to strings of symbols that are to be compared with stretches of the same length of a reference string comprising symbols. The above-mentioned string is identified here and hereinafter the present text with the expression "reference genome". For example, the "DNA fragments" expression could identify fragments of a polymer that must be aligned with each other to reconstruct a starting polymer (the polymer from which the aforementioned fragments are derived). For alignment purposes, each of said fragments is compared with multiple stretches of a reference polymer (in this case corresponding to the "reference genome").

BRIEF DESCRIPTION OF THE FIGURES

Further purposes and advantages of this disclosed system shall become clear from the following detailed description of an example of embodiment and from the annexed drawings, purely by way of explanation and non-limited to, in which.

DETAILED DESCRIPTION OF SOME EMBODIMENTS

In the following description, a FIG. may also be illustrated regarding elements not expressly indicated in that figure but in other figures. The scale and the proportions of the various elements depicted do not necessarily correspond to the real ones.

Figure 1:
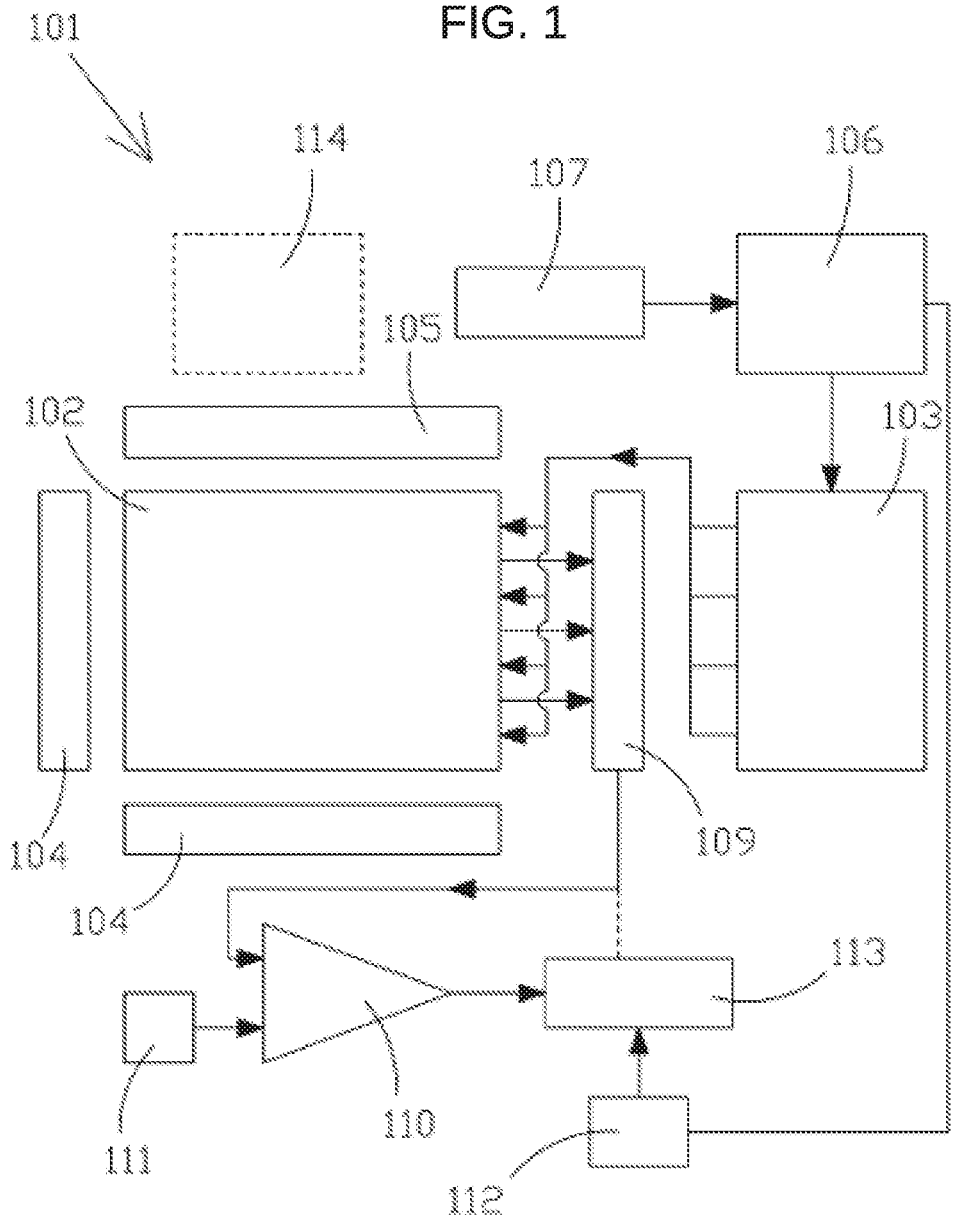
FIG. 1 shows, schematically, a comparison system according to the some embodiments.

FIG. 1 shows a comparison system 101, implemented in an integrated circuit, by means of which it is possible to compare one or more fragments of (a strand of) DNA with a strand of a reference genome for the entire length of the latter. For convenience, in the present description the expression "reference genome" shall mean a strand of the aforesaid reference genome. For each comparison between a DNA fragment and a stretch of the reference genome, system 101 determines whether the Hamming distance between said DNA fragment and the stretch of the genome with which it is compared is less than a threshold value settable by a user of the system. For each DNA fragment the system 101 produces as a result a list of positions in the reference genome corresponding to which the Hamming distance between said DNA fragment and the stretch of the genome starting from said position is less than threshold, as shall be better illustrated in the following description. As part of the sequencing of a DNA specimen to which the fragments being compared by system 101 belong, the above list of positions can be used to determine the alignment of the DNA fragments having the highest probability of matching the DNA specimen being sequenced.

There are four types of nucleotides present in the DNA, each nucleotide being encoded in the system 101 by a bit pair. Both the reference genome and the DNA fragments to be aligned are therefore encoded by ordered sequences of bit pairs, previously referred to as "first sequence of bit pairs" and "second sequence of bit pairs". In the following description, for a clearer presentation and to facilitate the understanding of the disclosed system, instead of referring to a comparison between said first and second sequence of bit pairs, reference could be made to the comparison between the respective stretches of DNA from which it was encoded, that is, reference could be made to a comparison between a stretch of the reference genome and a DNA fragment (or a fragment thereof) to align.

Before describing in detail the individual components of system 101, it is appropriate to illustrate its overall architecture to define the role of each component and to clarify the way in which these components interact with each other.

The "core" of the system 101 is constituted by a computational and storage array 102 (previously referred to as "first array") within which the comparison between the reference genome and the DNA fragments to be aligned (or sections of them) takes place. The array 102 is connected to an array of switches 103 (which may be also referred to as "second array") to convey into array 102 the reference genome, decoders and amplifiers 104 and 105 for writing in the array 102 the DNA fragments to be aligned. The array 103 is connected to at least one serializer 106, in turn connected to at least one first memory 107, preferably of the First In First Out (FIFO) type, which is suitable for storing a sequence of bit pairs encoding a nucleotide sequence of the reference genome.

Figure 2:
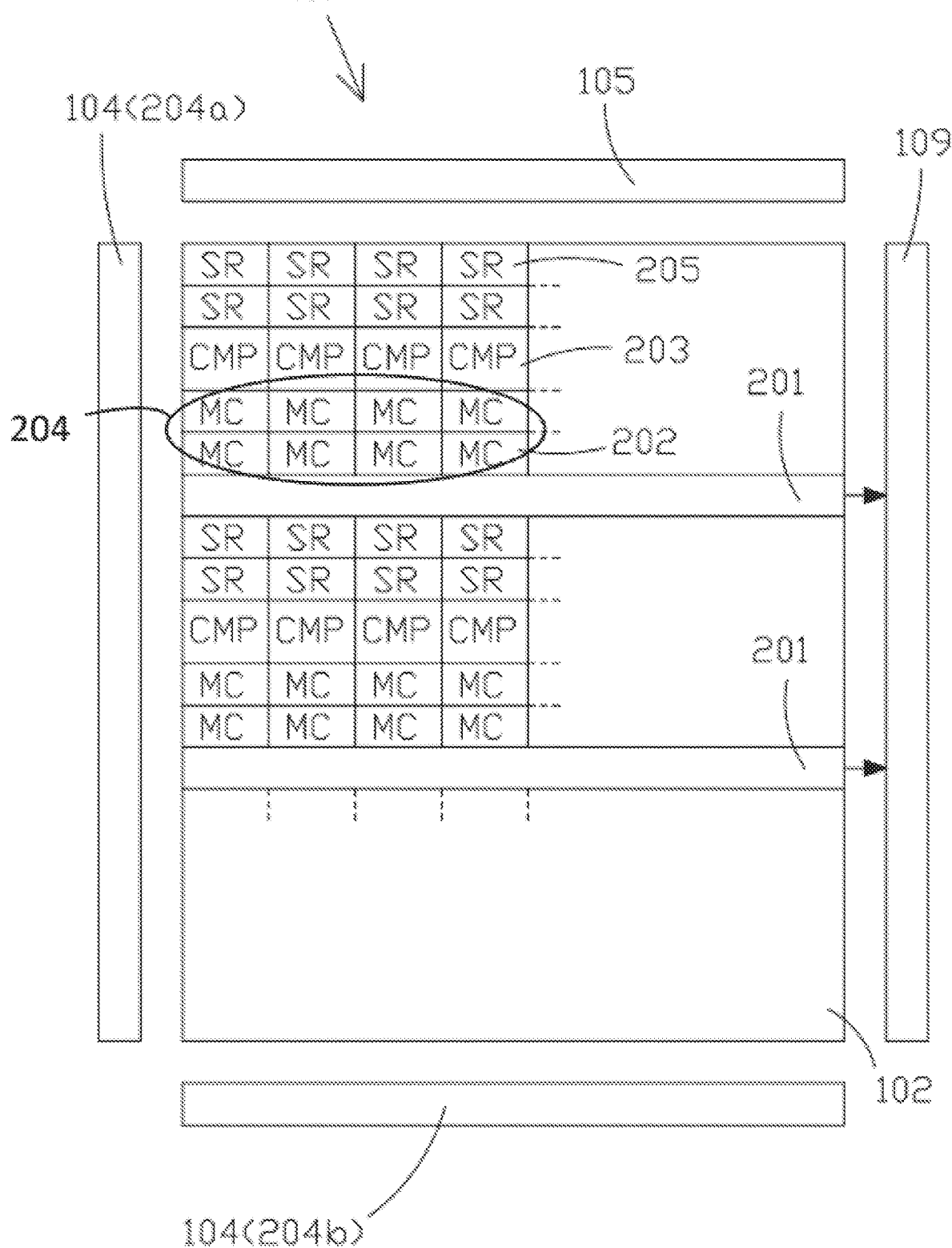
FIG. 2 shows, schematically, a computational and storage array included in the system in FIG. 1.

Furthermore, system 101 comprises CMP comparators visible in FIG. 2 (previously referred to as "first comparator") integrated in array 102 and suitable for comparing the reference genome's bit pairs with the bit pairs of a DNA fragment to align. The CMP comparators are connected to first adders 201 (visible in FIG. 2) integrated in array 102 and in turn connected to a second adder 109 external to array 102 for calculating the Hamming distance between a DNA fragment to be aligned (or a stretch of the same) and a stretch of the reference genome stored in array 102. The adder 109 is connected to a comparator 110 (previously referred to as "second comparator") to enable the comparison between the above-mentioned Hamming distance and a threshold value memorized in a register 111 which is also connected to the comparator 110.

Finally, system 101 also comprises a counter 112 connected to the serializer 106 and able to encode the position, within the reference genome, of each of the nucleotides corresponding to each of the bit pairs stored in array 102 from the serializer 106 via array 103. Counter 112 is also connected to a second memory 113, also preferably FIFO type, whose write enabling signal comes from comparator 110. In particular, said enabling event is such that the aforesaid position in the reference genome is memorized in memory 113 whenever the comparator 110 detects that the Hamming distance is less than the threshold value stored in register 111. Therefore, for each DNA fragment to be aligned, memory 113 stores the positions in the reference genome corresponding to which the Hamming distance between the DNA fragment and the genome stretch which originates from said position is less than said threshold. In other words, for each DNA fragment to be aligned, memory 113 stores the alignments of said fragment that have the highest probability of being correct.

In a variant of the comparison system, memory 113 stores not only the positions in the reference genome corresponding to which the Hamming distance between said DNA fragment and the genome stretch which originates from said position is less than said threshold, but also the Hamming distances (output from the adder 109) calculated in correspondence with the above positions. In this variant of the system, for each DNA fragment to be aligned, memory 113 stores not only the alignments of said fragment that have the highest probability of being correct, but also the Hamming distances corresponding with these alignments. The link existing between adder 109 and memory 113 is represented by dashed lines in FIG. 1. The aforesaid direct connection is only present in this variant of the disclosed system.

Considering the above, system 101 can compare directly (in an exact way, by means of brute force calculation) a DNA fragment with the reference genome for the entire length of the latter.

All the above-listed components of system 101 are controlled by a processor 114 capable of interfacing with components external to system 101 for retrieving both bit pairs sequences encoding the reference genome (to be inserted in memory 107), and bit pairs sequences encoding the DNA fragments to be aligned (to be inserted into array 102 through decoders 104 and amplifiers 105). More precisely, processor 114 is preferably capable of interfacing with a traditional computer (or "host") by appearing as a SRAM ("Static Random Access Memory") or standard DRAM ("Dynamic Random Access Memory"), or appearing as a device on a USB connection ("Universal Serial Bus") or PCIe ("Peripheral Component Interconnect Express") or other equivalent parallel or serial connections. In addition, or alternatively to this, processor 114 is capable of interfacing with a non-volatile mass memory in which one or more reference genomes are stored; such memory can be for example a FLASH/SSD drive ("Solid State Disk") or a magnetic media disk with an SATA type connection ("Serial AT Attachment") or SAS ("Serial Attached SCSI"). It is because of the length of the reference genome (on the order of billions of nucleotides), that this cannot be stored in its entirety within array 102 as the DNA fragments to be aligned; it is therefore necessary to use a "buffer" 107 accessed by serializer 106, to convey the reference genome into array 102.

Having the general architecture of system 101 been specified, the individual components cited above will now be described in detail starting from array 102.

Regarding FIG. 2, it is possible to note that array 102 comprises:

A plurality of pairs of shift registers 205, each of which includes a row of memory cells 202 capable of storing one bit (previously referred to as "first lines"), preferably SRAM type. These pairs of rows of memory cells 202 are suitable for storing a sequence of bit pairs that encode a sequence of nucleotides of the reference genome. Therefore, in each pair (in column) of memory cells of a pair of shift registers 205 a nucleotide of the reference genome is memorized.

A plurality of pairs of rows of one-bit memory cells 202 (previously referred to as "second lines"), preferably SRAM type and individually addressable for reading and writing. These pairs of rows 204 of memory cells 202 are suitable for storing a sequence of bit pairs encoding a nucleotide sequence of a DNA fragment to align. Therefore, in each pair (in column) of memory cells 202 of a pair of rows 204 of memory cells 202 one nucleotide of a DNA fragment to align is memorized. Preferably, array 102 comprises several pairs of rows 204 of memory cells 202 equal to the number of shift register 205 pairs;

A plurality of rows (previously referred to as "third rows") comprising the above-mentioned comparators 203. The latter are digital equality comparators between bit pairs, preferably with active low output. Each comparator 203 is connected to a pair (in column) of memory cells of a pair of shift registers 205 and to a pair (in column) of memory cells 202 of a pair of rows 204 of memory cells 202. Preferably, each comparator 203 is connected to a pair of memory cells of the shift register 205 and to a pair of memory cells 202 belonging to the same column (in array 102) to which the comparator 203 belongs. The comparators 203 are suitable for comparing a bit pair encoding a nucleotide of the reference genome (stored in the pair of memory cells of the shift registers 205) with a bit pair encoding a nucleotide of a DNA fragment to be aligned (stored in the pair of memory cells 202). Each comparator 203 produces an output signal 1 if the two-bit pairs compared (the two nucleotides) are different, and a 0 signal if the two-bit pairs are the same.

It is noted that a similar operation but with opposite polarity can equivalently be achieved using digital equality comparators between bit pairs having active high output. In this case, each comparator 203 output would produce a signal 0 if the two pairs of compared bits (the two nucleotides) are different and a signal 1 if the two-bit pairs are the same.

The comparator 203 belonging to the same row (of array 102) are also preferably connected to pairs (in column) of memory cells belonging to the same pair of SR registers, and to pairs (in column) of memory cells 202 belonging to the same pair of rows of memory cells 204. The comparators 203 of a row of array 102 are therefore suitable for comparing a reference genome stretch with a stretch of the DNA fragment to be aligned. Preferably, array 102 includes a row of comparator 203 for each pair of shift registers 205 (and consequently for each pair of rows 204 of memory cells 202).

Although the memory cells of the shift registers 205 and the memory cells 202 are preferably SRAM type, they could equivalently be DRAM, FLASH, or other memory type.

Solely for illustrative purposes, in FIG. 2 each row of comparator 203 is interposed between a pair of shift registers 205 (above) and a pair of rows 204 of memory cells 202 (below).

Figure 3:
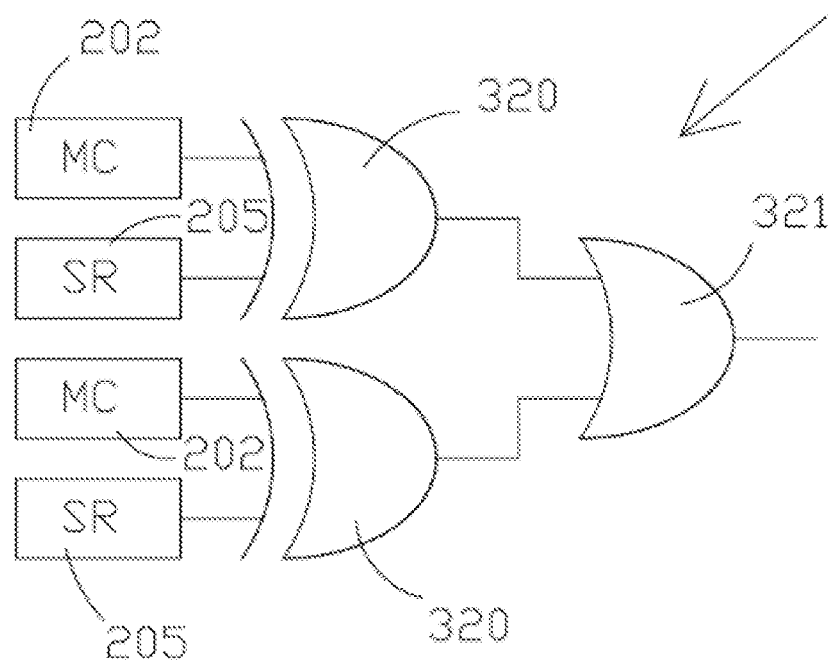
FIG. 3 shows, in more detail, some components of the computational and storage array in FIG. 2.

FIG. 3 shows a possible implementation of a comparator (CMP) 203 capable of comparing the contents of a pair of memory cells of a pair of shift registers 205 with the contents of a pair of memory cells 202. This includes two XOR gates 320 with two inputs and an OR gate 321 also with two inputs. The two inputs of one of the two XOR gates 320 are the bits stored in one of the two memory cells of one of the two shift registers 205 and the bit stored in the corresponding memory cell 202. The two inputs of the other XOR gate 320 are the other bit stored in the other memory cell of the other shift register 205 and the bit stored in the other memory cell 202. The two inputs of the OR 321 gate are the two outputs of the two XOR 320 gates.

It is noted that, if the comparator 203 were digital equality comparators between bit pairs having active high output (as previously mentioned), the comparator 203 would include a NOR gate instead of the OR gate 321.

Referring again to FIG. 2, it is possible to note that array 102 also comprises, for each row of comparator 203, a row of the above-mentioned adder 201. The latter are preferably digital adders connected to at least two comparators 203 belonging to the same column. More precisely, adders 201 are suitable for summing the output signals from two or more comparators 203 belonging to the same column. Since the comparators 203 have preferably an active low output, each adder 201 outputs a signal encoding a value corresponding to a Hamming distance (previously indicated as "first distance") between the reference genome stretch and the stretch of DNA fragment compared by the comparators 203 connected to said adder 201.

It is noted that, in an equivalent manner, if the comparators 203 were digital equality comparators between bit pairs having active high output (as previously mentioned), each adder 201 would output a signal encoding a value corresponding to the number of identical nucleotides between the reference genome stretch and the stretch of DNA fragment compared by comparators 203 connected to said adder 201.

The adders 201 belonging to the same row (of array 102) are preferably connected to comparators 203 belonging to the same row (of array 102). Each row of adders 201 of array 102 may comprise multiple adders 201, or a single adder 201 suitable for summing the output signals from all the comparators 203 belonging to the same row.

Solely for illustrative purposes, in FIG. 2 each row of adders 201 is placed below the pair of rows of MC memory cells connected to the comparators 203 line connected to the adders 201. The shift registers 205, the comparators 203 and the adders 201 are controlled by processor 114.

It is evident from the above description that array 102 comprises multiple sections at the same time performing computation and storage, each including a pair of shift registers 205, a pair of rows 204 of memory cells 202, a row of comparators 203 and a row of adders 201. For example, the rows of memory cells 202 and the shift registers 205 could have length equal to 100. A DNA fragment having length equal to 100 (comprising 100 nucleotides) can then be stored in each pair of rows of memory cells 202. For example, array 102 includes 10 of the above-mentioned sections.

Adder 109, controlled by processor 114, is preferably located on of one side of array 102. The latter is preferably a digital adder connected to adders 201 present in array 102. More precisely, adder 109 can sum the output signals from two or more adders 201.

The presence of the adder 109 is necessary because a DNA fragment to be aligned may have a length exceeding the length of a row of MC memory cells. In this case, the DNA fragment can be stored in array 102 on multiple pairs of rows of MC memory cells. Regarding the case in which each row of adders 201 of array 102 includes a single adder 201 suitable for summing the output signals from all the CMP comparators belonging to the same row, each adder 201 outputs only a "partial" distance between a stretch of the reference genome and the DNA fragment, which is a distance relevant to the portion of said DNA fragment stored on a pair of rows of MC memory cells. To calculate the distance of the entire DNA fragment (previously defined "second distance") it is necessary to add the partial distances calculated by adders 201. This sum can be carried out by adder 109.

The adder 109 is connected to comparator 110 through a multiplexer (not shown in the figures). This is a consequence of the fact that several DNA fragments to be aligned can be stored simultaneously in the array 102. In other words, as comprehensively illustrated in the present description, more DNA fragments can be simultaneously compared with the respective stretches of the reference genome. In this case, adder 109 can simultaneously sum up the partial distances calculated by adders 201 connected to the comparators 203 that compare the same DNA fragment with a portion of the reference genome. In other words, in case in array 102 two fragments of DNA to be aligned are simultaneously stored, adder 109 is able for adding together the partial distances calculated by adder 201 to simultaneously calculate the Hamming distances for both DNA fragments. However, the Hamming distances may not be sent simultaneously to comparator 110. It is for this reason that system 101 also comprises a multiplexer by means of which any multiple Hamming distances calculated simultaneously by adder 109 may be sent sequentially to comparator 110. In such case, memory 113 is also suitable for containing the alignments corresponding to which the Hamming distance is less than the threshold value, for each of the DNA fragments present simultaneously in array 102.

It is noted that, in case each row of adders 201 of array 102 includes a single adder 201 suitable for summing the output signals from all the comparators 203 belonging to the same row, when in array 102 a DNA fragment to be aligned is stored, that occupies only one pair of rows of memory cells 202, the partial distance calculated by the adder 201 coincides with the actual Hamming distance. The adder 109 therefore simply transmits to the comparator 110 the distance calculated by the adder 201, without summing it with any other partial distance.

As previously mentioned array 102 is connected to decoders 104 and to amplifiers 105, controlled by processor 114, to enable storing the DNA fragments to be aligned in array 102. The decoders 104 comprise a row decoder 204a and a column decoder 204b preferably and respectively on the remaining three sides of array 102. It is by means of decoders 104 that processor 114 selects the memory cell 202 or cells on which to perform a read or write operation. The amplifiers 105 are preferably located on the fourth side of array 102 and include an "input buffer" and "sense amplifier," amplifiers by means of which processor 114 can perform an operation of writing or reading on one or more memory cells 202, storing in the latter the bit pairs corresponding to the nucleotides of a DNA fragment to be aligned.

The storage of the reference genome in array 102 is instead carried out by serializer 106 and the array of switches 103, which are also controlled by processor 114. The presence of serializers 106 is made necessary by the fact that the output bus of memory 107 has width greater than two bits. Serializer 106 provides the array of switches 103 with a bit pair (a nucleotide in the reference genome) at a time instead of multiple bit pairs at once, as output by memory 107.

The array of switches 103 is connected to each pair of shift registers 205. More precisely, the array of switches 103 is connected to the pairs (in column) of end memory cells of each pair of shift registers 205, to the pairs of memory cells of the input and output of each pair of shift registers 205. As known, in the shift registers 205, for each clock pulse the bits scroll from one cell to the adjacent one, from the input cell of the chain towards the output cell of the same. Unlike with the memory cells 202, it is therefore not necessary to write in all the shift registers 205 of memory cells. It is sufficient to progressively write bit pairs (in column) into each pair of input memory cells of shift registers 205. Array 103 allows storing in each pair of input memory cells of a pair of shift registers 205 either an output bit pair from the serializer 106 or a bit pair stored in a pair of output memory cells of another pair of shift registers 205.

Figure 4:
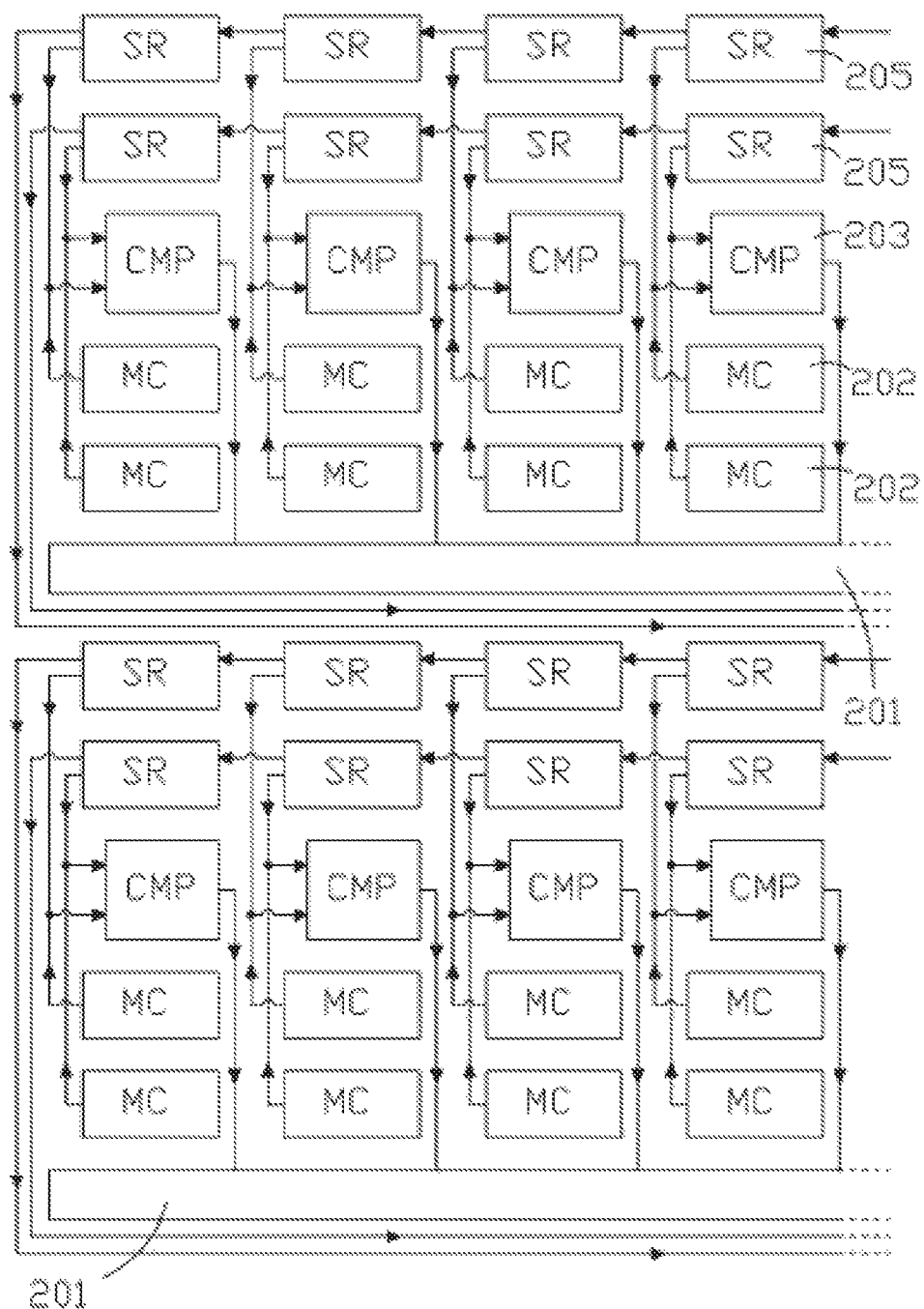
FIG. 4 shows, schematically, other components of the computational and storage array in FIG. 2.

As shown in FIG. 4, array 103 therefore allows connecting two pairs of SR registers so that, for each clock pulse, the bit pair stored in the pair of output memory cells of one of the two pairs of SR registers, scrolls into the pair of input memory cells of the other pair of registers. In other words, array 103 allows connecting two pairs of SR registers so that a shift of a sequence of bit pairs (coding a sequence of the reference genome nucleotides) can continue from a pair of SR registers to another pair of SR registers.

Figure 5:
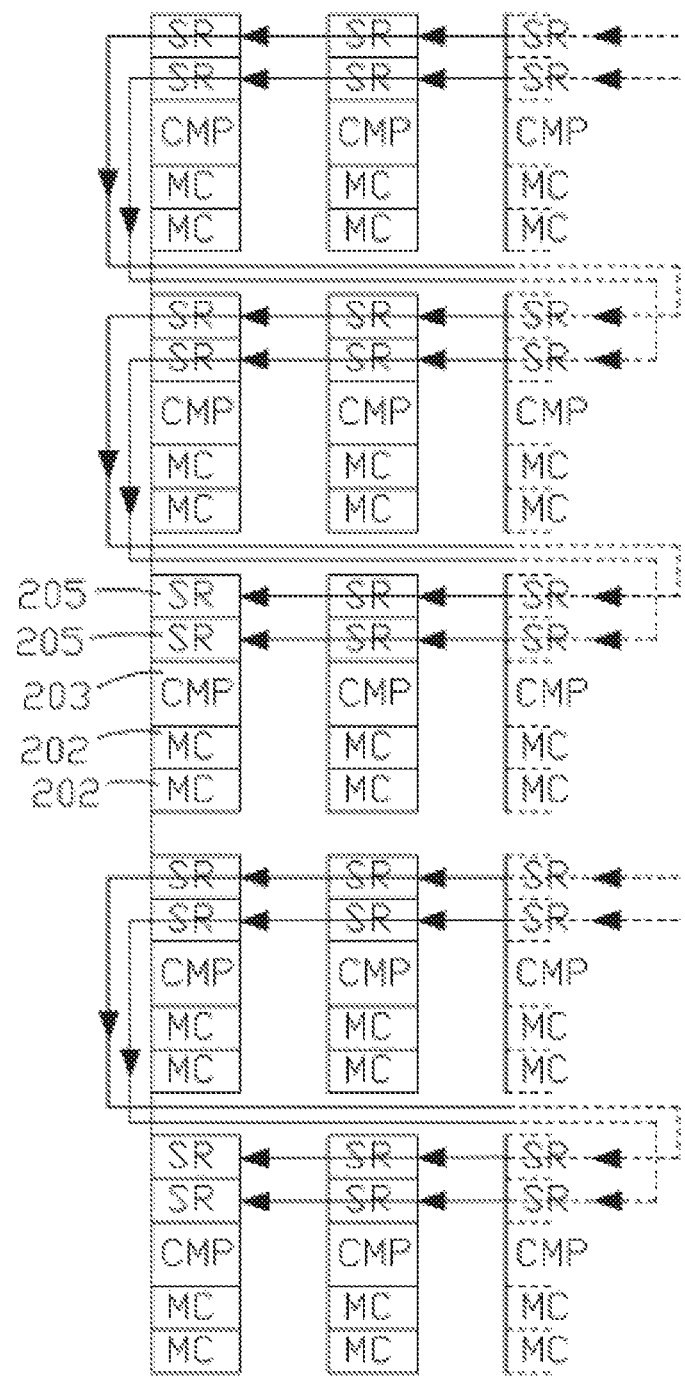
FIG. 5 shows a method of use of the computational and storage array in FIG. 2.

As shown in FIG. 5, array 103 also allows partitioning array 102. Array 102 can be divided into two or more parts to which the output from the serializer 106 can be sent simultaneously. In this way, the reference genome can be made to scroll simultaneously in multiple parts of the array, each comprising several the aforesaid sections that can be decided by a user of system 101. Considering this, it is preferable that system 101 includes a plurality of serializers 106, and even more preferably a serializer 106 for each of the above-mentioned sections of array 102.

In summary, thanks to the array of switches 103, a user of system 101 may decide not to perform any partition of array 102 (for example, because the DNA fragment to be aligned is so long as to occupy all pairs of memory cells 202) and scroll the reference genome from the first to the last pair of shift registers 205. A user of system 101 may on the contrary decide to make a partition of array 102 to match each part of array 102 for each of the above-mentioned sections (for example, because the DNA fragments to be aligned have a length less than twice the length of the pairs of rows of memory cells 202) and scroll the reference genome simultaneously in each part of array 102. In an intermediate situation, a user of system 101 may decide to make a partition of array 102 to match each part of array 102 to one or more sections of memory and calculation, depending on the size of the DNA fragments to be aligned.

All the above considerations are equivalently valid in the case in which system 101 includes a plurality of arrays 102 a controlled single processor 114.

Having now described system 101 as an entire system, before describing some variants, we shall illustrate the way in which system 101 is used to compare a DNA fragment with a reference genome for the entire length of the latter. For convenience, assume that the DNA fragment has a length equal to the number of available pairs of memory cells 202 (that it fills all the pairs of rows of memory cells 202), and that array 102 is not subjected to any partitioning. It is therefore sufficient to use only one serializer 106. The example of operation will now be illustrated starting from a configuration in which no nucleotides are stored in array 102.

Processor 114 begins to stream the reference genome into memory 107. Serializer 106 receives from the latter bit pairs encoding the nucleotides of the reference genome and transmits them, in sequence, to array 103 which, for each clock pulse, stores them in the input pair of memory cells of the first pair of shift registers 205. This way, the reference genome scrolls within the array 102 until it reaches the output memory cells of the last pair of shift registers 205. Meanwhile, counter 112 encodes the position of the last bit pair (the last nucleotide) stored in array 102 occupied in the reference genome. Thereafter processor 114 stores the DNA fragment to be aligned in pairs of memory cells 202 of array 102 via decoders 104 and amplifiers 105. The comparators 203 compare the bit pairs stored in the memory cells of the shift register 205 with the bit pairs stored in the corresponding memory cells 202. Adder 201 calculates the "partial" Hamming distance for each section of array 102. Adder 109 calculates the "overall" Hamming distance between the DNA fragment and the stretch of reference genome currently stored in the shift registers 205. Comparator 110 compares the Hamming distance calculated by adder 109 with the threshold value stored in register 111. If said distance is less than the threshold value, the position indicated by counter 112 is stored in memory 113. Processor 114 then commands serializer 106 to output a bit pair, to scroll by one position the reference genome in array 102 and update counter 112. The described procedure is then repeated until the reference genome scrolls entirely into array 102. After said scroll, the process can be repeated for a second DNA fragment to be aligned.

Therefore, for each DNA fragment to be aligned, system 101 enables comparing the threshold value with the Hamming distance between the DNA fragment and each stretch of the reference genome having the same length as the DNA fragment. For each DNA fragment, system 101 produces a list of alignments (of positions in the reference genome) in relation to which the above-mentioned Hamming distance is less than the threshold value, a list of alignments for which the greater the probability that they are correct.

The procedure described above is implementable in an equivalent manner in the case where the length of the DNA fragments to be aligned is such as to allow the simultaneous storage in array 102 of a plurality of the above-mentioned fragments. In such case, stretches of the reference genome are compared simultaneously with multiple DNA fragments. As mentioned previously, in these cases adder 109 simultaneously calculates the Hamming distance for each of the DNA fragments present in array 102. These distances are sent in sequence to comparator 110 through a multiplexer. Memory 113 contains in this case the alignments corresponding to which the Hamming distance is less than the threshold value, for each of the DNA fragments present simultaneously in array 102.

In case a DNA fragment to be aligned has a length not corresponding to a multiple of the length of the pairs of rows of MC memory cells, said fragment is truncated at the highest multiple. In other words, if the fragment to be aligned is for example about two and a half times the length of the pairs of rows of memory cells 202, said fragment is truncated to memorize in array 102 a stretch of length equal to two times the length of the pairs of rows of memory cells 202.

The above procedure is also feasible in an equivalent manner in the case in which array 102 is partitioned by means of the switches of array 103. In this case, counter 112 must encode of the position of each of the serializers 106 in the reference genome.

Regarding the remaining FIGS. 6 to 13, some possible variants of system 101 will now be illustrated. These variants are not alternatives. That is, they may coexist in the comparison system.

Figure 6:
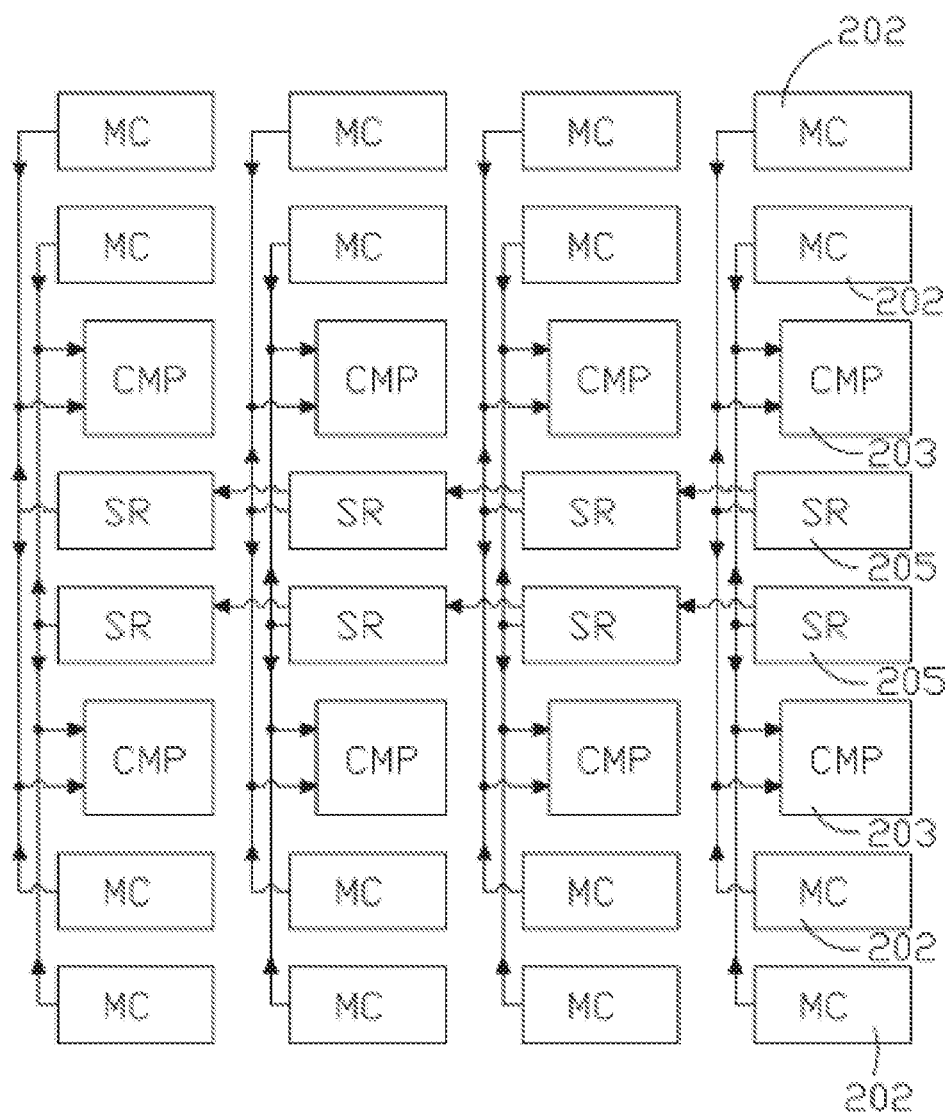
FIG. 6 shows, schematically, a detail of a first variant of the system in FIG. 1.

FIG. 6 refers to a comparison system that differs from system 101 in that array 102 comprises, for each pair of shift registers 205, a plurality of pairs of rows of memory cells 202 and a plurality of rows of comparators 203. Preferably, the number of pairs of rows of memory cells 202 is equal to the number of lines of comparators 203. In this variant of the system, a reference genome stretch stored in a pair of shift registers 205 is simultaneously comparable with a plurality of sections of respective DNA fragments stored in the pairs of rows of memory cells 202.

Figure 7:
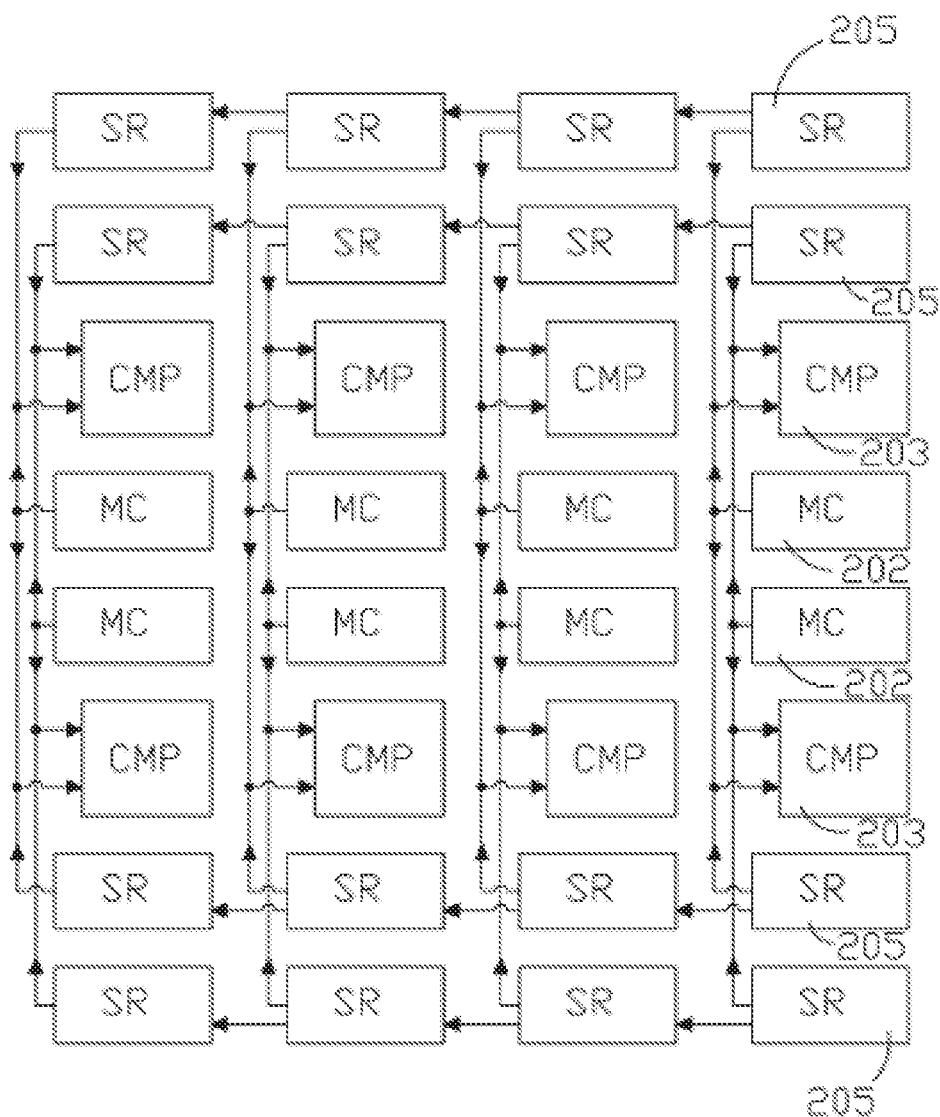
FIG. 7 shows, schematically, a detail of a second variant of the system in FIG. 1.

FIG. 7 refers to a comparison system that differs from system 101 in that, for each pair of rows of memory cells 202, array 102 comprises a plurality of pairs of shift registers 205 and a plurality of rows of comparators 203. Preferably, the number of pairs of shift registers 205 is equal to the number of rows of comparators 203. In this variant of the system, a portion of a DNA fragment stored in a pair of rows of memory cells 202 is simultaneously comparable with a plurality of stretches of the reference genome stored in the pairs of shift registers 205. More precisely, by splitting the reference genome in two partially overlapping sections and partitioning array 102, it is possible to simultaneously scroll the two sections of the reference genome into two parts of the array and simultaneously compare the same DNA fragment with said sections.

Figure 8:
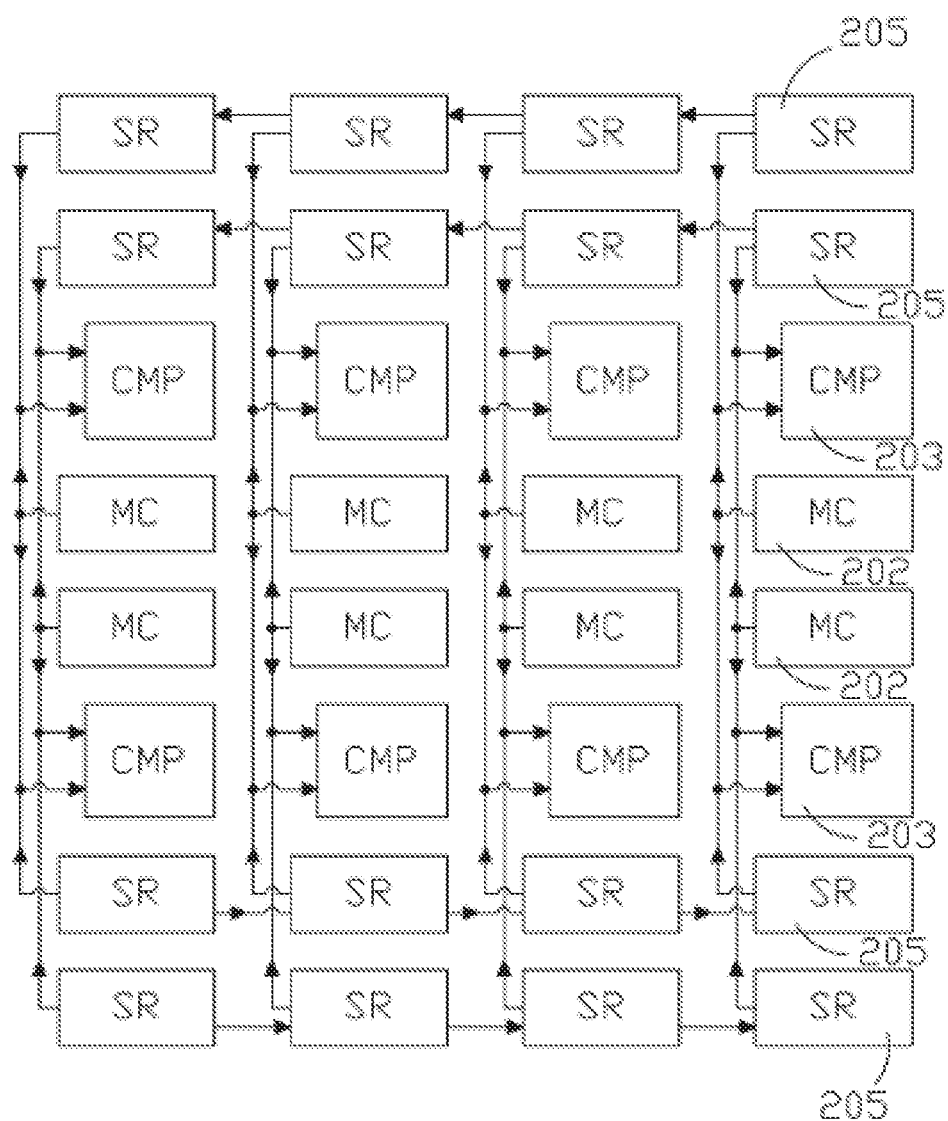
FIG. 8 shows a mode of use of a third variant of the system in FIG. 1.

FIG. 8 refers to a comparison system that, similarly to that shown in FIG. 7, differs from system 101 in that array 102 comprises, for each pair of rows of memory cells 202, a plurality of pairs of shift registers 205 and a plurality of rows of comparators 203. Preferably, the number of pairs of shift registers 205 is equal to the number of rows of comparators 203. The system in FIG. 8, however, differs from system 101 also in that it comprises a suitable logic to convert the reference genome in its complement to be stored in array 102 in the reverse direction. Said logic is well within reach of a technician skilled in the art, therefore we shall not dwell on implementation details. In this variant of the disclosed system, by means of a partition of array 102 a section of a DNA fragment stored in a pair of rows of memory cells 202 is simultaneously comparable with at least a stretch of the reference genome stored in a pair of shift registers 205 and with at least a stretch of the complement of the reference genome stored in another pair of shift registers 205. Regarding the case in which array 102 includes two pairs of shift registers 205 and a pair of rows of memory cells 202, since the complement of a reference genome must be read in reverse order, it is made to scroll by processor 114 in a pair of shift registers 205 in the opposite direction to that in which the reference genome is made to scroll in the other pair of shift registers 205. The above-mentioned logic for converting the reference genome into its complement is connected to each pair of shift registers 205 in which the reference genome is made to scroll in the opposite direction, between array 103 and the pair of shift registers 205.

Figure 9:
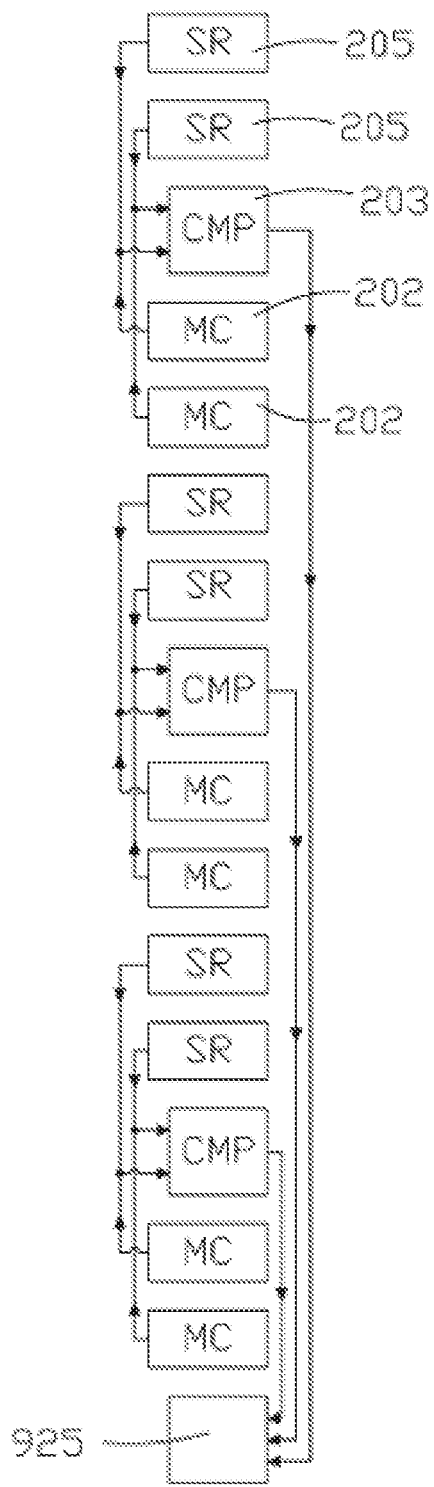
FIG. 9 shows, schematically, a detail of a fourth variant of the system in FIG. 1.

FIG. 9 refers to a comparison system that differs from system 101 in that array 102 comprises, every three lines of comparators 203, a fourth row of aggregators 925 consisting of OR gates, each with three inputs and one output. Each aggregator 925 receives as input three signals respectively coming from three comparators 203 belonging to different rows but preferably belonging to the same column (array 102) to which aggregator 925 belongs.

As known, a comparison of a DNA fragment to be aligned and a reference genome can be made, instead nucleotides-wise, codon-wise, in terms of triplets of nucleotides. This variant of the disclosed system lends itself to carry out the codon-wise comparison. To this end, the storage of the DNA fragment to be aligned and of the reference genome takes place in a slightly different way from that described for system 101. Instead of being done for pairs of rows, the storage is carried out for groups of three pairs of rows. The three nucleotides of each codon are stored in three pairs of memory cells belonging to the same column of array 102. In other words, regarding the DNA fragment to be aligned, the first nucleotide of the codons is stored in the first pair of rows of memory cells 202, the second nucleotide of the codons is stored in the second pair of rows of memory cells 202 and the third nucleotide of the codons is stored in the third pair of rows of the memory cells 202. Similarly, the first nucleotide of codons of the reference genome is stored in the first pair of shift registers 205, the second nucleotide of the codons is stored in the second pair of shift registers 205 and the third nucleotide of the codons is stored in the third pair of shift registers 205. Aggregators 925 are therefore suitable for comparing the codons of a DNA fragment to be aligned with the codons of the reference genome. Each aggregator 925 produces an output signal 1 if the compared codons are different and a 0 signal if the compared codons are equal.

Aggregators 925 belonging to the same row (of array 102) are also connected to sets of comparators 203 belonging to the same three lines. Aggregators 925 of a row of array 102 are therefore suitable for comparing the codons of a stretch of the reference genome with a stretch of the DNA fragment to be aligned.

For purely illustrative purposes, in FIG. 9 each row of aggregators 925 is located below the three sections of array 102 to which aggregators 925 are connected.

Furthermore, for each row of aggregators 925, the comparison system illustrated in FIG. 9 comprises a row of third adders (not shown in the figure) preferably digital and connected to at least two aggregators 925 belonging to the same row. More precisely, the third adders are suitable for summing the output signals from two or more aggregators 925 belonging to the same row. Since aggregators 925 consist of OR gates, each third adder produces at its output a signal encoding a value corresponding to a Hamming distance between the codons in the stretch of reference genome and in the DNA fragment to be aligned, aggregated by aggregators 925 connected to said third adder.

The third adders belonging to the same row (of array 102) are preferably connected to aggregators 925 belonging to the same row (of array 102). Each row of third adders of array 102 may comprise a single third adder or multiple third adders capable of summing the output signals from all aggregators 925 belonging to the same row. Aggregators 925 and third adders are controlled by processor 114.

On the side of array 102 where adder 109 is located, a fourth adder (not shown in the figure), controlled by processor 114, is also instanced. Said fourth adder is preferably digital and connected to third adders present in array 102. More precisely, said fourth adder is suitable for summing the output signals from two or more third adders.

Similarly, to what was said for adder 109, the presence of the fourth adder is required by the fact that a DNA fragment can be stored in array 102 on more triads of rows of memory cells 202. Regarding the case where each row of third adders of array 102 includes a single third adder capable of summing the output signals from all the aggregators 925 belonging to the same line, each third adder output produces only a "partial" distance in codons between a stretch of the reference genome and the DNA fragment. To calculate the distance in codons for the entire DNA fragment it is necessary to sum the partial distances in codons calculated by the third adders. This sum can be carried out by the fourth adder.

Similarly, to adder 109, the fourth adder is connected to comparator 110 to compare the Hamming distance in codons, and the threshold value stored in register 111. Similarly, to what was said for system 101, the comparison system illustrated in FIG. 9 includes the counter 112 connected to serializer 106 and able to encode the position of each of the codons of the reference genome that can be stored in array 102 through array 103. Counter 112 is connected to memory 113, preferably FIFO type, which is enabled by comparator 110. Said enabling signal is such that the aforesaid position in the reference genome is stored in memory 113 whenever comparator 110 detects that the Hamming distance in codons is lower than the threshold value stored in register 111. For each DNA fragment to be aligned, memory 113 stores the positions in the reference genome in correspondence of which the Hamming distance in codons between said DNA fragment and the stretch of the genome that originates from said position is less than said threshold. In other words, the alignments for each DNA fragment to be aligned, that have the highest probability of being correct are stored in memory 113.

Similarly, to adder 109, the fourth adder is connected to comparator 110 through a multiplexer (not shown in the figures). This is a consequence of the fact that multiple DNA fragments to be aligned can be stored simultaneously in array 102. In other words, multiple DNA fragments can be simultaneously compared with the respective stretches of the reference genome. In this case, the fourth adder is suitable for summing simultaneously the partial distances in codons calculated by third adders connected to aggregators 925 which compare codons in the same DNA fragment with a stretch of the reference genome. For example, regarding the case where two fragments of DNA to be aligned are simultaneously stored in array 102, the fourth adder is suitable for summing the partial distances in codons calculated from third adders to calculate simultaneously the Hamming distance in codons for both DNA fragments. The Hamming distances in codons may however not be sent simultaneously to comparator 110. It is for this reason that the comparison system also includes a multiplexer through which any multiple Hamming distances in codons calculated simultaneously by the fourth adder may be sent in sequence to comparator 110. In this case, memory 113 is also suitable for storing the alignments in relation to which the Hamming distance in codons is less than the threshold value, for each of the DNA fragments present simultaneously in array 102.

It is noted that, when each row of third adders of array 102 includes a single third adder capable of summing the output signals from all the aggregators 925 belonging to the same row, and when a DNA fragment to align that occupies only one pair of rows of memory cells 202 is stored in array 102, the partial distance in codons calculated by the third adder coincides with the actual Hamming distance in codons. The fourth adder therefore simply transmits to comparator 110 the distance in codons calculated by the third adder, without summing it to any other partial distance in codons.

Figure 10:
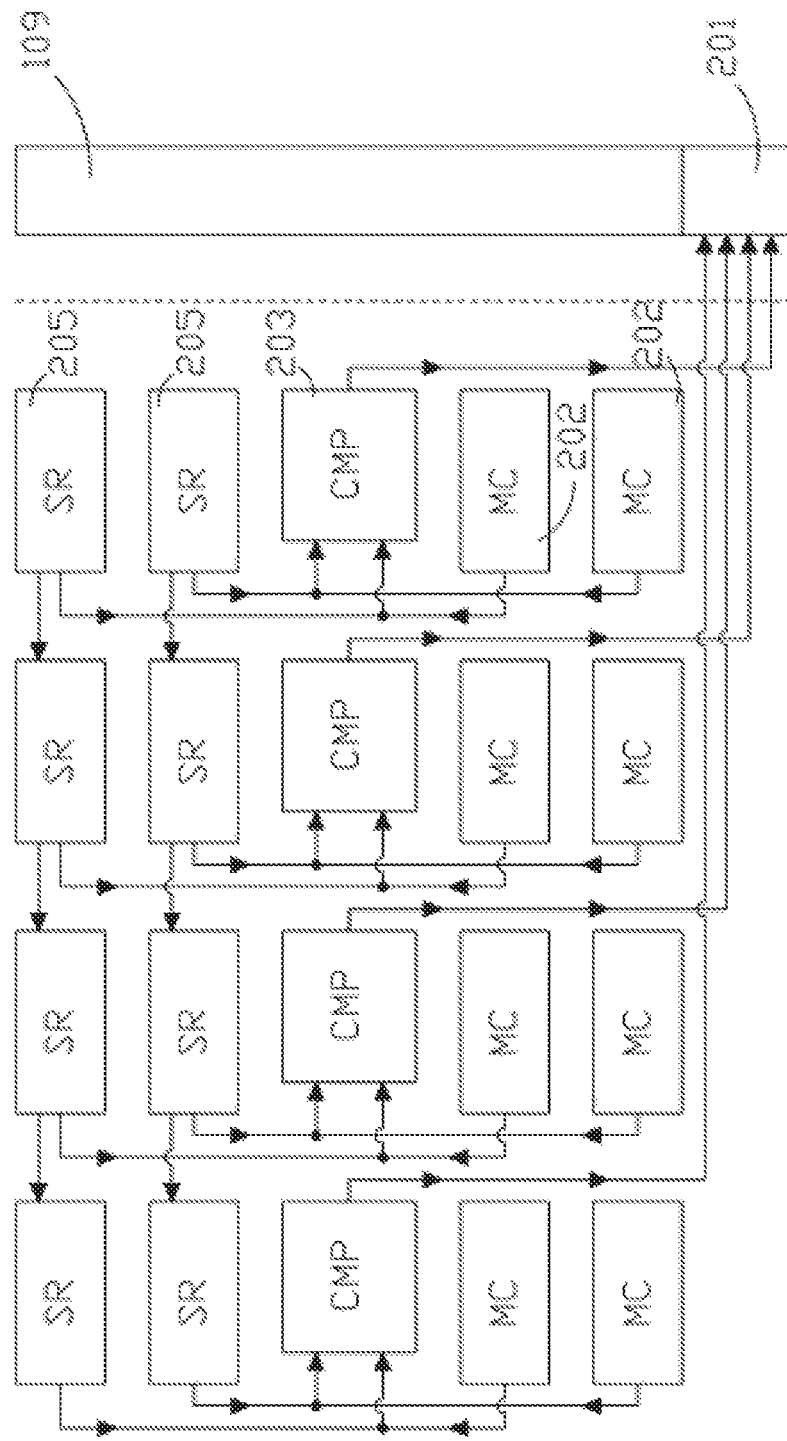
FIG. 10 shows, schematically, a detail of a fifth variant of the system in FIG. 1.

FIG. 10 illustrates a comparison system that differs from system 101 in that adders 201 are housed outside of array 102. Similarly, with reference to the system 101, the system according to the present variant may comprise, for each row of comparators 203, multiple adders 201, or a single adder 201 suitable for adding up the output signals from all the comparators 203 belonging to the same row.

The above is applicable in an equivalent manner to the comparison system illustrated in FIG. 9 (in which the comparison between a DNA fragment to align and a stretch of the reference genome is also feasible for codons). The third adders, instead of being integrated in array 102, may be housed outside it. The comparison system may include, for each row of aggregators 925, multiple third adders or a single third adder capable of summing the output signals from all aggregators 925 belonging to the same row.

Figure 11:
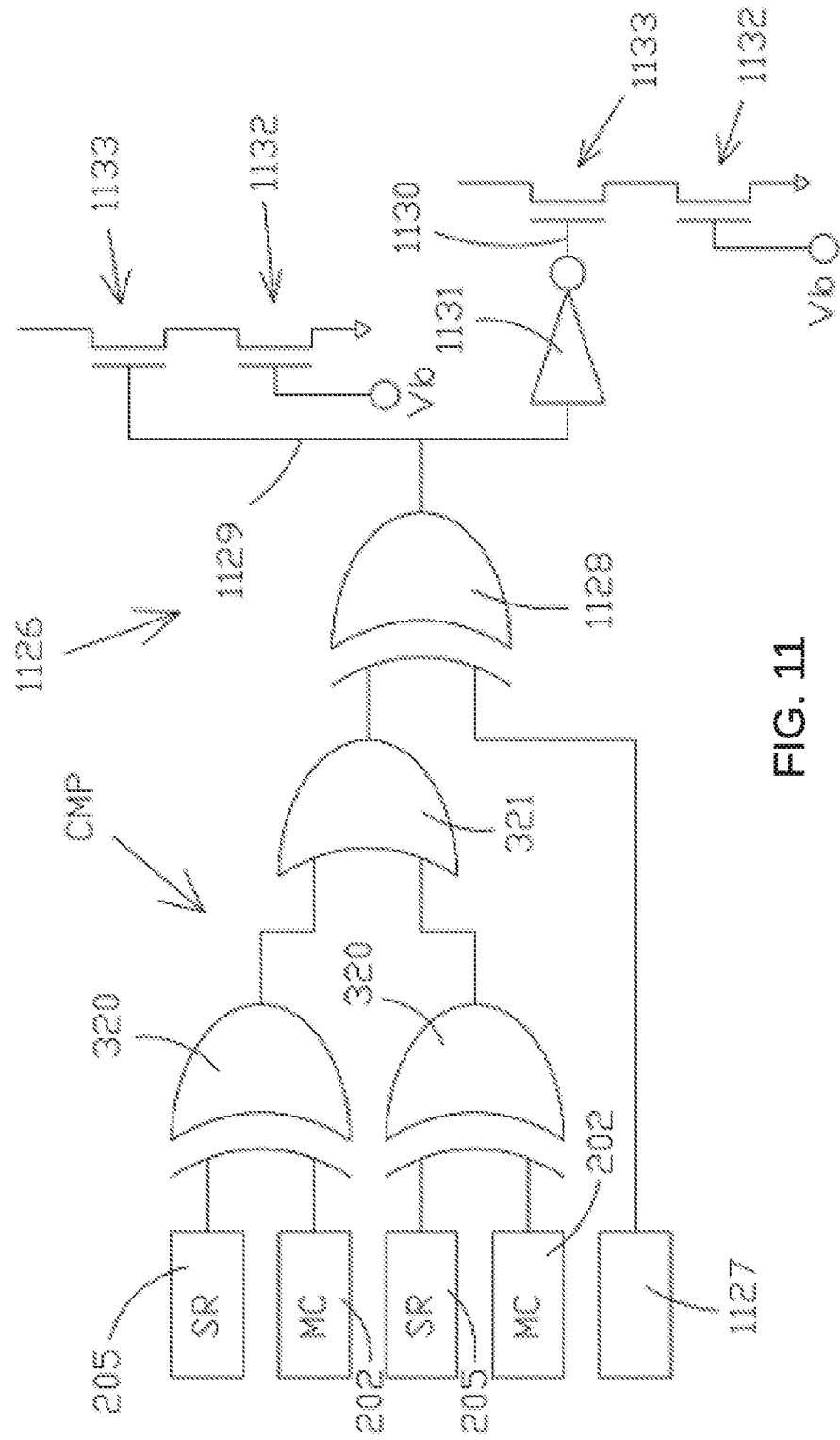
FIG. 11 shows, schematically, a detail of a sixth variant of the system in FIG. 1.
Figure 12:
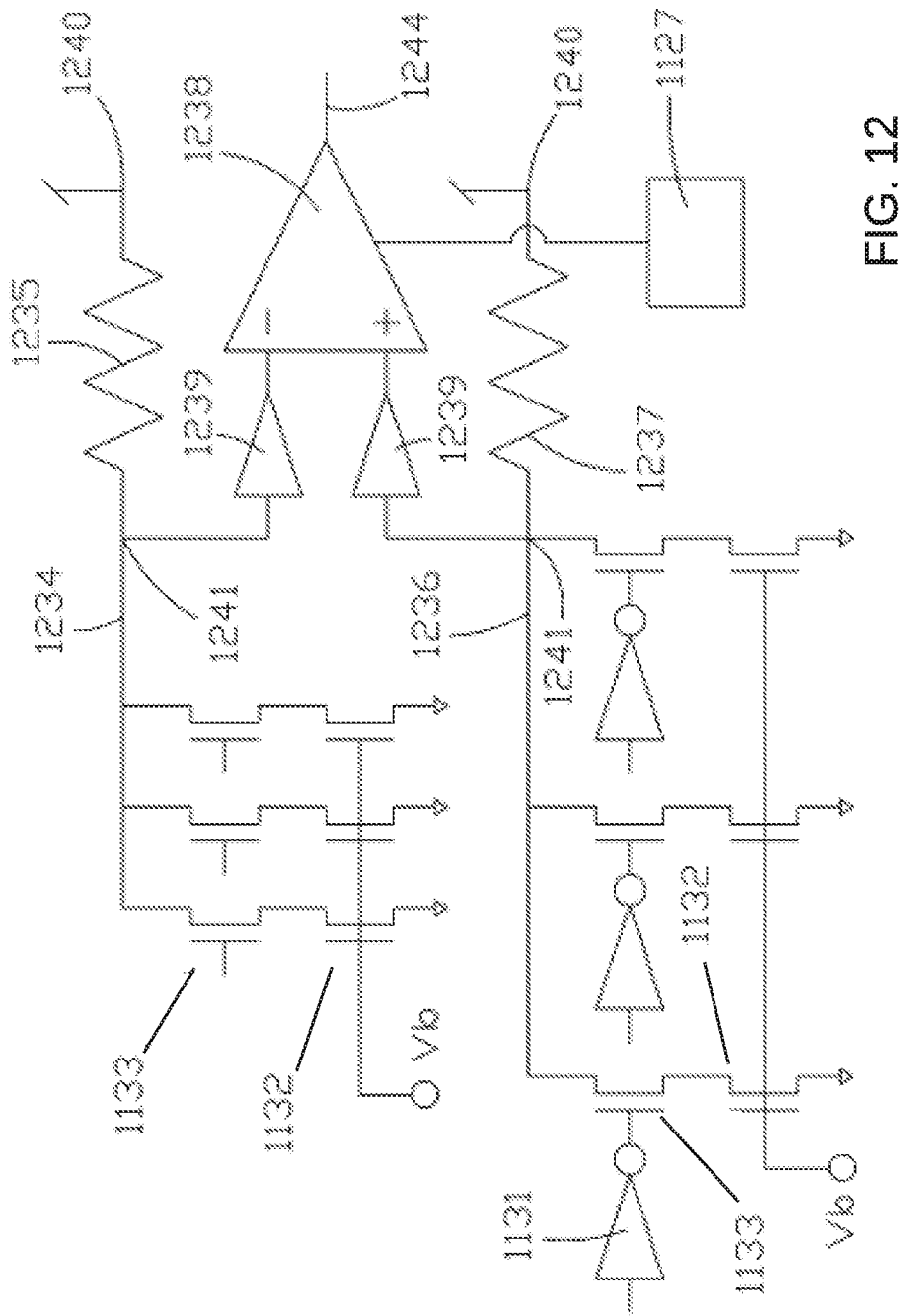
FIG. 12 shows, schematically, a detail of another variant of FIG. 11.

FIGS. 11 and 12 illustrate a comparison system that differs from system 101 in that the adders consider 201 and consider 109 are suitable for adding up, at least in part, in an analog mode, the output signals from the comparators 203. Performing the sums in analog mode allows strongly reducing the area of the adders in the case of implementation as an application-specific integrated circuit (ASIC). This allows a better overall utilization of the area in terms of memory capacity.

In this case, for each comparator 203, there comprises circuit architecture 1126 able to compensate, at least partially, for the systematic and random errors naturally associated with an analog summation process. Regarding FIG. 11, the "compensating means" 1126 for each comparator 203 comprise:

A phase line 1127 suitable for transmitting, for each clock pulse of processor 114, a high phase signal followed by a signal of low phase or vice versa;

An XOR gate 1128 with two inputs and one output. The XOR gate 1128 receives as input signals the phase line 1127 and the output signal from the CMP comparator;

A positive output line 1129 and a negative output line 1130 resulting from a bifurcation of the output line from the XOR gate 1128. The negative output is obtained by means of an inverter 1131, placed along line 1130;

For each of the two output lines 1129 and 1130, a first MOSFET 1132 in "current mirror" configuration connected in series to a second MOSFET 1133 in "pass gate" configuration driven by the output line 1129 or 1130.

According to the present variant, the comparison system includes a single adder 201 for each row of CMP comparators. Accordingly, regarding FIG. 12, each adder 201 comprises:

a first current-sum line 1234 connected to MOSFET 1133 driven by the positive output lines 1129 of the CMP comparators belonging to the same row associated to said adder 201;

a second current-sum line 1236 connected to the MOSFET 1133 driven by the negative output lines 1130 of said comparator CMP belonging to the same row associated to aforesaid adder 201.

Adder 109 comprises:

for each adder 201, a first and a second load resistor 1235 and 1237 connected at a first terminal 1240 to a known voltage (for example that of the power supply circuit) and at a second terminal 1241 to a circuit 1238 suitable for calculating, for each clock pulse of processor 114, the difference between voltage at resistor 1237 and voltage at resistor 1235. Preferably, along the connection between each terminal 1241 of the resistors 1235 and 1237 and the circuit 1238, a unity-gain voltage amplifier 1239 is instanced;

a third array of switches (not shown in the figure) connected to both circuits 1238 and array 102.

That third array is suitable for:

connecting to each other, corresponding to a first node, at least two of the first current-sum line 1234;

connecting to each other, corresponding to a second node, at least two of the second current-sum line lines 1236;

For each circuit 1238, connecting terminal 1241 of resistor 1235 to one of the first current-sum line 1234 (as shown in FIG. 12) or to said first node, and connecting terminal 1241 of resistor 1237 to one of the second current-sum lines 1236 (as shown in FIG. 12) or to said second node.

Circuit 1238 receives the phase line 1127 to be suitable for calculating not only the difference between a voltage on resistor 1237 and a voltage on resistor 1235, but also the difference between the values measured during the two phases.

For simplicity, FIG. 12 shows schematically a single adder 201 connected to a single circuit 1238 of adder 209.

Adder 109 is connected to comparator 110 so that the latter can compare output signal 1244 from at least one of the circuits 1238 (suitably digitized by an analog-digital converter not shown in the figure) with the threshold value stored in register 111.

When a DNA fragment to be aligned is stored in array 102 to occupy a single pair of rows of memory cells 202, the third array connects directly the sum lines 1234 and 1236 associated with the comparators 203 which carry out the comparison of the DNA fragment with a stretch of the reference genome, to circuit 1238 associated to said lines of comparators 203. The output signal from said circuit 1238 is compared, by comparator 110, with the threshold value stored in register 111 via a multiplexer.

When a DNA fragment to be aligned is stored in array 102 to occupy multiple pairs of rows of memory cells 202, the third array interconnects the sum lines 1234 and 1236 connected to the rows of comparators 203 performing the comparison of DNA fragment with a stretch of the reference genome. The sum lines 1234 and 1236 thus interconnected are in turn connected to one of the circuits 1238 related to these lines of the comparators 203. The output signal from said circuit 1238 connected to the current-sum lines 1234 and 1236, is compared, by comparator 110, with the threshold value stored in register 111 via a multiplexer.

When multiple DNA fragments to be aligned are stored simultaneously in array 102 (when multiple fragments of DNA are simultaneously compared with respective stretches of the reference genome), for each of said DNA fragments the third array interconnects the sum lines 1234 and 1236 related to the rows of the comparators 203 performing the comparison of said DNA fragment with a stretch of the reference genome. For each of said DNA fragments, the sum lines 1234 and 1236 thus interconnected are in turn connected to one of the circuits 1238 related to these lines of comparators 203. The adder 109 is then suitable for generating simultaneously signals coding the Hamming distances between the fragments stored in array 102, and respective stretches of the reference genome. The Hamming distances may be sent in sequence to comparator 110 via a multiplexer. In this case, memory 113 is suitable for storing the alignments in correspondence to which the Hamming distance is less than the threshold value, for each of the fragments of DNA simultaneously present in array 102.

The calculation of a differential voltage across circuit 1238 allows cancelling, at least partially, some error sources such as external noise sources or variations in oxide thickness with which the gate is realized in the MOSFET 1132. The partial compensation of the errors is enhanced by phase line 1127 which, during each clock cycle, swaps the positive output line 1129 with the negative output line 1130.

Figure 13:
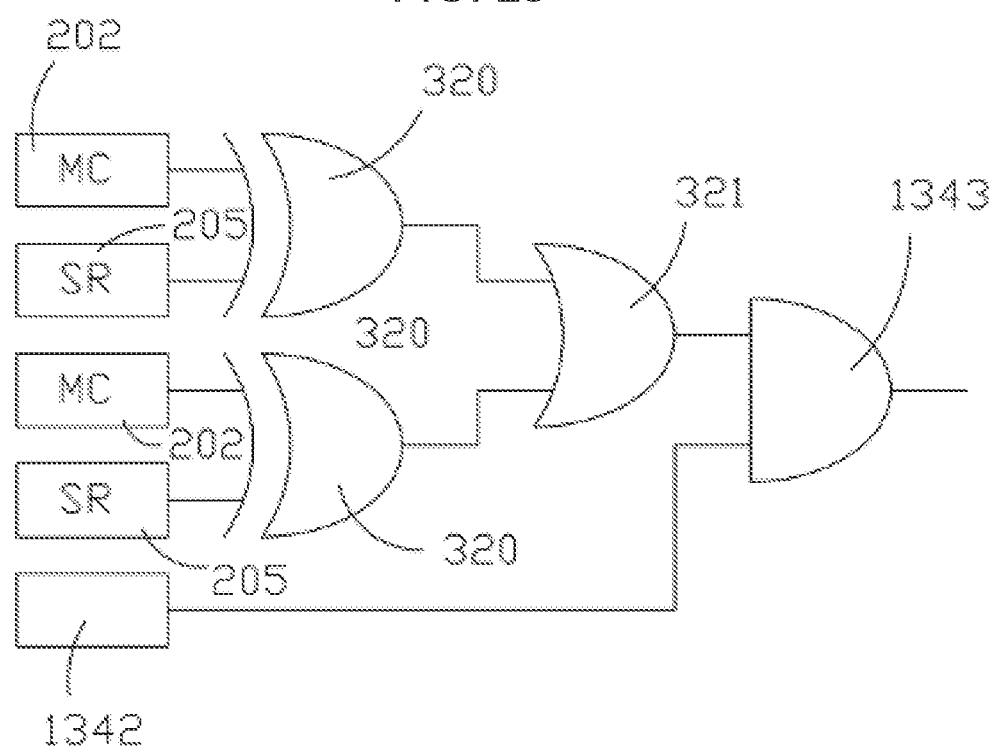
FIG. 13 shows, schematically, a detail of a seventh variant of the system in FIG. 1.

In a first variant of the disclosed system, compared to the system illustrated in FIGS. 12 and 13, the compensation means are devoid of phase line 1127 and XOR gate 1128. In this case, the positive output line 1129 and the negative output line 1130 result from a bifurcation of the output line of the comparator 203.

In a second variant of the disclosed system, in addition to being devoid of the phase line 1127 and the XOR gate 1128, the comparison system is also devoid of the positive output lines 1129. In other words, there is no bifurcation of the output line of the comparator 203, which is to correspond to the negative output line 1130. Not having the positive output lines 1129, the comparison system is also devoid of sum lines 1234, resistors 1235 and circuitry 1238. In addition to that, said third array of switches, instead of being connected to circuitry 1238, is connected directly to terminal 1241 of resistors 1237 and is suitable for:

connecting them, at a first node, at least two of the second current-sum lines 1236;

connecting terminal 1241 to one of the second current-sum lines 1236 (as shown in FIG. 12) or to said first node.

Adder 109 is connected to comparator 110 so that the latter can compare the voltage value on at least one of the resistors 1237 with the threshold value stored in register 111.

According to this variant of the comparison system, when a DNA fragment to be aligned is stored in array 102 to occupy a single pair of rows of memory cells 202, the third array connects directly the sum line 1236 related to the comparators 203 which carry out the comparison of said DNA fragment with a stretch of the reference genome, to resistor 1237 related to such comparators 203. The voltage value at said resistor 1237 is compared, by comparator 110, with the threshold value stored in the register 111 through a multiplexer.

When a DNA fragment to be aligned is stored in array 102 such that it occupies multiple pairs of rows of memory cells 202, the third array interconnects the sum lines 1236 related to the rows of comparators 203 which carry out the comparison of said DNA fragment with a stretch of the reference genome. The sum lines 1236 so interconnected are in turn connected to one of the resistors 1237 related to these lines of comparators 203. The voltage value on resistor 1237 that is connected to the sum lines 1236 is to be compared with the threshold value stored in the register 111, by comparator 110 via a multiplexer.

When multiple DNA fragments to be aligned are stored simultaneously in array 102 (when multiple fragments of DNA are simultaneously compared with respective stretches of the reference genome), for each of said DNA fragments the third array interconnects the sum lines 1236 which are related to the rows of the comparators 203 comparing said DNA fragment with a stretch of the reference genome. For each of said DNA fragments, the sum lines 1236 thus interconnected are in turn connected to one of the resistors 1237 related to these lines of comparators 203. The adder 109 is then suitable for generating simultaneously the signals encoding the Hamming distances between the fragments stored in array 102, and the respective stretches of the reference genome. The Hamming distances may be sent in sequence to comparator 110 via a multiplexer. In this case, memory 113 is suitable for storing the alignments in correspondence to which the Hamming distance is less than the threshold value, for each of the fragments of DNA simultaneously present in array 102.

What was said about the comparison system illustrated in FIGS. 11 and 12 is applicable in an equivalent manner to the variant of the disclosed system illustrated in FIG. 9 (in which the comparison between a DNA fragment to be aligned and a stretch of the reference genome is also feasible for codons). In this case, the third adder and the fourth adder are suitable for summing, at least in part, by analogy, the output signals from aggregators 925. For each aggregator 925, there comprises a circuit architecture (not shown in the figures) able to compensate, at least partially, the systematic and random errors naturally associated with an analog summation process. For each aggregator 925 the "compensating means" include:

a phase line suitable to transmit, for each clock pulse of processor 114, a high phase signal followed by a low phase signal or vice versa;

an XOR gate with two inputs and one output. The XOR gate receives in input the signal of the phase line and the output signal from aggregator 925;

a positive output line and a negative output line resulting from a bifurcation of the output line from the XOR gate. The negative output is obtained via an inverter placed on the negative output line;

For each of the two output lines, a first MOSFET in a "current mirror" configuration connected in series to a second MOSFET in "pass-gate configuration" driven by the output line.

According to the present variant, the comparison system includes a single third adder for each row of aggregators 925. In those circumstances, each third adder comprises:

a first current-sum line connected to the second MOSFET driven by the positive output lines of aggregators 925 belonging to the same row related to said third adder;

a second current-sum line connected to the second MOSFET driven by the negative output lines of aggregators 925 (belonging to the same row related to said third adder).

The fourth adder comprises:

for each third adder, a first and a second load resistor connected at a first terminal to a known voltage (for example that of the power supply circuit) and at a second terminal to a circuit suitable for calculating, for each clock pulse of processor 114, the difference between a voltage of the second resistor and a voltage of the first resistor. Preferably, along the connection between each second terminal of the resistors and the above circuit there is an unitary-gain voltage amplifier;

a third array of switches (not shown in the figures) is connected both to the aforesaid circuits and to array 102. The third array is suitable for:

interconnecting, corresponding to a first node, at least two of the first current-sum lines;

interconnecting corresponding to a second node, at least two of the second current-sum lines.

For each of the above circuits, connecting the second terminal of the first resistor to one of the first current-sum lines or said first node, and connecting the second terminal of the second resistor to one of the second current-sum lines to said second node.

The above circuit receives the phase line to be suitable for calculating not only the difference between a voltage at the second resistor and a voltage across the first resistor, but also the difference between the values measured during the two phases.

The fourth adder is connected to comparator 110 so that the latter can compare the output signal from at least one of said circuits with the threshold value stored in register 111.

When a DNA fragment to be aligned is stored in array 102 to occupy a single pair of three rows of MC memory cells, the third array directly connects the first and the second current-sum lines related to aggregators 925 performing the comparison in codons between said DNA fragment and a stretch of the reference genome, to the circuit related to the aforesaid aggregators 925. The output signal from said circuit is compared, by comparator 110, with the threshold value stored in the register 111 via a multiplexer.

When a DNA fragment to be aligned is stored in array 102 to occupy multiple triads of pairs of rows of memory cells 202, the third array interconnects the first and second current-sum lines related to the rows of aggregators 925 which perform the comparison in codons of said DNA fragment with a stretch of the reference genome. The sum lines so interconnected are in turn connected to one of the circuits related to the above lines of aggregators 925. The output signal from the circuit that is connected to the sum lines is to be compared by comparator 110, with the threshold value stored in register 111 via a multiplexer.

When several DNA fragments to be aligned are stored simultaneously in array 102 (when multiple fragments of DNA are simultaneously compared with stretches of the respective reference genome), for each of said DNA fragments the third array interconnects the first and second current-sum lines connected to the rows of aggregators 925 which perform the comparison in codons of said DNA fragment with a stretch of the reference genome. For each of said DNA fragments, the sum lines so interconnected are in turn connected to one of the circuits related to these lines of aggregators 925. The fourth adder is therefore suitable for simultaneously generating the signals coding the Hamming distances in codons between the fragments stored in array 102, and the respective stretches of the reference genome. The Hamming distances in codons may be sent in sequence to comparator 110 via a multiplexer. In this case, memory 113 is suitable for storing the alignments in correspondence to which the Hamming distance in codons is less than the threshold value, for each of the fragments of DNA simultaneously present in array 102.

Similarly, to what was described previously, in a first variant of the disclosed system, the compensation means of the comparator system described above do not have the phase line and the XOR gate associated with it. In this case, the positive output line and the negative output line result from a bifurcation of the output line aggregator 925.

In another variant of the disclosed system, the comparison system, in addition to being devoid of the phase line and the XOR gate related to with it is also devoid of the positive output lines. In other words, there is no bifurcation of the output line of aggregator 925, which is to correspond to the negative output line. Not having the positive output lines, the comparison system is also devoid of the first current-sum lines, of the first resistors and of suitable circuits for calculating a voltage difference. In addition to that, said third array of switches, instead of being connected to the aforesaid circuits, is connected directly to the second terminals of the second resistors and is suitable for:

connecting between them, at a first node, at least two of the second current-sum lines;

connecting a second terminal to one of the second current-sum lines or to said first node.

The fourth adder is connected to comparator 110 so that the latter can compare the voltage value of at least one of the second resistors with the threshold value stored in register 111.

According to this variant of the comparison system, when a DNA fragment to be aligned is stored in array 102 such that it occupies a single pair of three rows of memory cells 202, the third array connects directly the sum line related to aggregators 925 which perform the comparison in codons of said DNA fragment with a stretch of the reference genome, to the resistor related to the aforesaid aggregators 925. The voltage value of said resistor is compared by comparator 110, with the threshold value stored in register 111 via a multiplexer.

When a DNA fragment to be aligned is stored in array 102 such that it occupies multiple triads of pairs of rows of MC memory cells, the third array interconnects the sum lines related to the rows of aggregators 925 which perform the comparison in codons of said DNA fragment with a stretch of the reference genome. The sum lines so interconnected are in turn connected to one of the second resistors related to these lines of aggregators 925. The voltage value on the resistor that is connected to the sum lines is compared by comparator 110, with the threshold value stored in register 111 via a multiplexer.

When several DNA fragments to be aligned are stored simultaneously in array 102 (when multiple fragments of DNA are simultaneously compared with the respective stretches of the reference genome), for each of said fragments of DNA the third array connects the sum lines related to the rows of aggregators 925 performing the comparison in codons, of said DNA fragment with a stretch of the reference genome. For each of said DNA fragments, the sum lines so interconnected are in turn connected to one of the second resistors related to these lines of aggregators 925.

The fourth adder is therefore suitable for simultaneously generating the signals coding the Hamming distances in codons between the fragments stored in array 102, and the respective stretches of the reference genome. The Hamming distances in codons may be sent in sequence to comparator 110 via a multiplexer. In this case, memory 113 is suitable for storing the alignments in correspondence to which the Hamming distance in codons is less than the threshold value, for each of the fragments of DNA simultaneously present in array 102.

FIG. 13 refers to a comparison system that differs from the system 101 in that array 102 comprises, for each pair of rows of memory cells 202, a further row of memory cells 1342, preferably SRAM type and individually addressable for reading and writing Array 102 further comprises, for each row of comparators 203, another row of AND gates 1343 with two inputs and one output. Each of the AND gates 1343 receives an output bit input from one of the comparators 1343 and the bit contained in one of the memory cells 1342.

Similarly, to what was said regarding the memory cells of the SR registers and the memory cells 202, although the memory cells 1342 are preferably SRAM type, they could equivalently be DRAM or FLASH type.

Preferably (as shown in FIG. 13), array 102 comprises several pairs of rows of memory cells 202 equal to the number of pairs of shift registers 205, equal to the number of lines of comparators 203, equal to the number of rows of memory cells 1342 and equal to the number of lines of AND gates 1343.

Preferably, the AND gates 1343 belonging to the same row (of array 102) are connected to the comparators 203 belonging to the same row and to the memory cells 1342 belonging to the same row related to the pair of rows of memory cells 202 compared by said comparator 203. Even more preferably, each AND gate 1343 is connected to the comparator 203 and to the memory cell 1342 belonging to the same column (array 102) which belongs to AND gate 1343.

According to the present variant, adders 201 of the comparison system are connected to at least two AND gates 1343 belonging to the same line, instead of comparators 203. More precisely, the adders 201 are suitable for summing the output signals from two or more AND gates 1343 belonging to the same row. The adders 201 belonging to the same row (of array 102) are preferably connected to AND gates 1343 belonging to the same row (of array 102). Each row of adders 201 of array 102 may comprise multiple adders 201 or a single adder 201 suitable for summing the output signals from all AND gates 1343 belonging to the same row.

Reading and writing operations can be performed on the memory cells 1342 by processor 114 through the decoders 104 and the amplifiers 105 of array 102.

As known, an AND gate produces an output signal 1 if the input bits are both 1, and a 0 signal otherwise. The AND gates 1343, being connected to the pairs of memory cells 202 by means of comparators 203, therefore allow to disable, when necessary, a pair of memory cells 202 just by setting to 0 the bit contained in the memory cell 1343 connected to it (to ensure the Hamming distance cannot be increased). This means that, in case a DNA fragment to be aligned having a length not corresponding to a multiple of the length of the pairs of rows of memory cells 202, said fragment must not be truncated to an integer multiple. The portion of unused pairs of rows of memory cells 202 can be disabled by setting 0 in the memory cells 1342 connected to them. In other words, if the fragment to be aligned is for example, about two and a half times the length of the pairs of rows of memory cells 202, said fragment is memorized in three pairs of rows of memory cells 202 by disabling the second half of the third pair of rows of memory cells 202.

The presence of the memory cells 1342 offers a further advantage. When the confidence of correct recognition (also known as "Phred quality score") of one or more nucleotides within a DNA fragment to be aligned is low, in known direct-alignment systems the DNA fragment is truncated or discarded. According to this variant of the comparison system o, by storing 0 in the memory cells 1342 corresponding to nucleotides with a low recognition confidence, it is possible to individually exclude these nucleotides, without having to truncate or discard the fragment of DNA.

Considering what has been said, it appears evident that the system 101 can be implemented in an integrated circuit in which computing resources are suitably compenetrated with memory resources to make a direct comparison possible between a set of DNA fragments to be aligned and a reference genome in a period less than with known systems.

In the present description, the "integrated circuit" expression means, in an equivalent manner, a custom integrated circuit (known as "Application Specific Integrated Circuit" or ASIC) or a programmable logic array (known as "Field-programmable Gate Array" or FPGA).

The above description being provided for one or more example embodiments, it is obvious that some changes may be introduced by one of ordinary skill in the art.

The invention claimed is:

1. A system for comparing at least one DNA fragment to a reference genome, the system comprising:
   at least a first computational-memory array, including:
      a plurality of pairs of shift registers (SR) each of which comprises a first row of one-bit memory cells; cells, said first rows of each said pair of SRs being suitable to accommodate a first sequence of bit pairs encoding a sequence of nucleotides of said reference genome;
      a plurality of pairs of rows of one-bit memory cells (MC), individually addressable in writing and reading, each said pair of said rows of MCs being suitable to accommodate a second sequence of bit pairs encoding a sequence of nucleotides of said DNA fragment;
      a plurality of rows of first digital equality comparators (CMPs) for bit pairs, each of said CMPs being suitable to compare a bit pair of said first sequence to a bit pair of said second sequence, said CMPs belonging to the same said row and being suitable to compare bit pairs of the same said first sequence to bit pairs of the same said second sequence, for each said row, at least a first adder of output signals from at least two of said CMPs belonging to said; row, each said first adder being suitable to generate an output signal encoding a value corresponding to a plurality of first distances between at least a length of said first sequence and a corresponding length of said second sequence compared by the CMPs, which said output signals received from the comparison of the CMPs are to be input to said first adder;
      at least a second adder of two or more of said first distances suitable to generate an output signal encoding a value corresponding to a second distance; and
      at least a second comparator suitable to compare said second distance to a threshold value; and
   a hardware-based processor to control at least one of a writing operation and a reading operation in said MCs of said rows of MCs, and to control an operation of said pairs of SRs, said CMPs, said second comparator, said first adders, and said second adder.

2. The comparison system according to claim 1, wherein said pairs of SRs are couplable to each other so that a scrolling of said first sequence of bit pairs is to continue from one of said pairs of SRs to another said pair of SRs.

3. The comparison system according to claim 2, further comprising:
   at least one serializer suitable to provide output bit pairs of said first sequence; and
   a second array of switches coupled both to said serializer and to said first array, said second array being suitable to allow, for each said pair of SRs, housing in two end memory cells of said first rows of one of said pairs of SRs one of the output bit pairs from said serializer or a bit pair housed in two of the end memory cells of said first rows of another said pair of SRs, said hardware-based processor being suitable to control an operation of said serializer and said second array.

4. The comparison system according to claim 2, further comprising:
   a counter suitable to generate output information encoding the position in said reference genome of each of said nucleotides corresponding to each of said bit pairs of said first output sequence from said serializer; and
   a memory coupled to said counter and to said second comparator, said memory being suitable to store said output information from said counter whenever said second comparator detects that said second distance is less than said threshold; value, said hardware-based processor being suitable to control an operation of said counter.

5. The comparison system according to claim 1, wherein said first array comprises, for each said pair of SRs, a plurality of said pairs of rows of MCs, and a plurality of said rows of CMPs, and
   said first sequence housed in said pair of SRs is configured to be simultaneously comparable to a plurality of said second sequences of bit pairs housed in said pairs of rows of MCs by said respective rows of CMPS.

6. The comparison system according to claim 1, wherein said first array comprises, for each said pair of rows MCs, a plurality of said pairs of SRs, and a plurality of said rows of CMPs, and said second sequence of bit pairs housed in said pair of rows of MCs are configured to be simultaneously comparable to a plurality of said first sequences of bit pairs housed in said pairs of SRs by said respective rows of CMPs.

7. The comparison system according to claim 6, characterized in that said pairs of registers (SR) are controllable by said processor so that a scrolling of said first sequence of bit pairs in one of said pairs of registers (SR) occurs in the opposite direction to a scrolling of said first sequence of bit pairs in another said pair of registers (SR).

8. The comparison system according to claim 7, characterized in that it comprises at least one conversion logic of said reference genome into a genome which is complementary thereto,
   said comparison system further comprising, for each said pair of second rows of memory cells (MC), two of said pairs of registers (SR), wherein said scrolling of said respective first sequences of bit pairs occurs in opposite direction, said first sequences of bit pairs encoding a nucleotide sequence of said reference genome and a nucleotide sequence of said genome which is complementary to said reference genome, respectively.

9. The comparison system according to claim 1, wherein said pairs of SRs are configured to be controllable by said hardware-based processor so that a scrolling of said first sequence of bit pairs in one of said pairs of registers (SR) is to occur in the opposite direction to a scrolling of said first sequence of bit pairs in another said pair of SRs.

10. The comparison system according to claim 1, characterized in that said first array further comprises:
   every three said third rows of first comparators (CMP), a fourth row of aggregators with OR gate having three inputs and one output, each said aggregator receiving as input three output signals from three said first comparators (CMP) belonging to said three third rows, respectively,
   said comparison system further comprising:
   for each said fourth row, at least a third adder of output signals from at least two of said aggregators belonging to said fourth row;
   each said third adder being suitable for generating an output signal encoding a value corresponding to a third distance;
   at least a fourth adder of two or more of said third distances and suitable for generating an output signal encoding a value corresponding to said second distance;

said processor being suitable for controlling the operation of said aggregators, said third adders and said fourth adder.

11. The comparison system according to claim 10, characterized in that said third adders and said fourth adder are suitable for at least partially adding said output signals from said aggregators in an analog manner.

12. The comparison system according to claim 11, characterized in that it comprises, for each said aggregator, compensation means for at least partially compensating for systematic and random errors naturally associated with an analog summation process, said compensation means comprising:
- a positive output line and a negative output line resulting from a bifurcation of an output line from said aggregator, said negative output being obtained by means of an inverter;
- for each of said output lines, a first MOSFET current mirror coupled in series to a second MOSFET of NMOS or PMOS type, said second MOSFET being driven by said output line,
- each said third adder comprising:
- a first current summation line coupled to said second MOSFETs driven by said positive output lines of said aggregators belonging to the same said fourth row;
- a second current summation line coupled to said second MOSFETs driven by said negative output lines of said aggregators belonging to the same said fourth row;
- said fourth adder comprising:
- for each said fourth line, a first and a second load resistor coupled at a first end to a known voltage and at a second end to a circuit suitable for calculating, at each clock pulse of said processor, the difference between a voltage on said second resistor and a voltage on said first resistor;
- a third array of switches coupled to both said circuits and to said first array, said third array being suitable for:
- coupling together at least two of said first current summation lines at a first node;
- coupling together at least two of said second current summation lines at a second node;
- for each said circuit, coupling said second end of said first resistor to one of said first current summation lines or to said first node, and coupling said second end of said second resistor to one of said second current summation lines or to said second node,
- said second comparator being suitable for comparing an output voltage signal from at least one of said circuits to said threshold value,
- said processor being suitable for controlling the operation of said compensation means.

13. The comparison system according to claim 1, wherein at least one of said first adders and third adders, when present, are at least partially housed within said first array.

14. The comparison system according to claim 1, characterized in that said first adders and said second adder are suitable for at least partially adding said output signals from said first comparators (CMP) in an analog manner.

15. The comparison system according to claim 14, characterized in that it comprises, for each said first comparator (CMP), compensation means for at least partially compensating for systematic and random errors naturally associated with an analog summation process, said compensation means comprising:
- a positive output line and a negative output line resulting from a bifurcation of an output line from said first comparator (CMP), said negative output being obtained by means of an inverter;
- for each of said output lines, a first MOSFET current mirror coupled in series to a second MOSFET of NMOS or PMOS type, said second MOSFET being driven by said output line,
- each said first adder comprising:
- a first current summation line coupled to said second MOSFETs driven by said positive output lines of said first comparators (CMP) belonging to the same said third row;
- a second current summation line coupled to said second MOSFETs driven by said negative output lines of said first comparators (CMP) belonging to the same said third row;
- said second adder comprising:
- for each said third line, a first and a second load resistor coupled at a first end to a known voltage and at a second end to a circuit suitable for calculating, at each clock pulse of said processor, the difference between a voltage on said second resistor and a voltage on said first resistor;
- a third array of switches coupled to both said circuits and to said first array, said third array being suitable for:
- coupling together at least two of said first current summation lines at a first node;
- coupling together at least two of said second current summation lines at a second node;
- for each said circuit, coupling said second end of said first resistor to one of said first current summation lines or to said first node, and coupling said second end of said second resistor to one of said second current summation lines or to said second node,
- said second comparator being suitable for comparing an output voltage signal from at least one of said circuits to said threshold value,
- said processor being suitable for controlling the operation of said compensation means.

16. The comparison system according to claim 1, characterized in that said first array further comprises:
- for each said pair of second rows, a further row of memory cells with bits individually addressable in writing and reading;
- for each said third row, a further row of AND gates with two inputs and one output, each of said AND gates receiving as input an output bit from one of said first comparators (CMP) and the bit contained in one of said memory cells of said further row;
- said AND gates belonging to the same said row receiving as input output bits from said first comparators (CMP) belonging to the same said third row and bits contained in said memory cells of the same said further row associated to said pair of second rows compared by said first comparators (CMP);
- said first adders, for each said third row, being adders of output signals from at least two of said AND gates belonging to said further row corresponding to said third row.

17. The comparison system according to claim 1, wherein said hardware-based processor is suitable to interface with a host appearing as an SRAM memory or as a DRAM memory or as a peripheral device on USB connections or as a peripheral device on PCIe connections.

18. The comparison system according to claim 1, wherein said hardware-based processor is suitable to interface with a non-volatile memory in which at least said reference genome is stored.

\* \* \* \* \*